(12) United States Patent
Doty et al.

(10) Patent No.: US 11,833,108 B2
(45) Date of Patent: Dec. 5, 2023

(54) TERMINAL STERILIZATION FILTRATION CLOSED LYOPHILIZATION IN A CONTAINER

(71) Applicants: BAXTER INTERNATIONAL INC., Deerfield, IL (US); BAXTER HEALTHCARE SA, Glattpark (CH)

(72) Inventors: Mark Joseph Doty, Grayslake, IL (US); Christine L. Rebbeck, Lake Barrington, IL (US); Sydney Jean Cope, Chicago, IL (US); William Spencer Hurst, Burlington, WI (US); Grant Anthony Bomgaars, Kildeer, IL (US); Yuanpang Samuel Ding, Long Grove, IL (US); Thomas Edward Dudar, Palatine, IL (US); Ying-Cheng Lo, Long Grove, IL (US); Mark Edward Pasmore, Grayslake, IL (US); Michael Joseph Sadowski, Ringwood, IL (US); Anastasios Hristakos, Evanston, IL (US); Joseph Vincent Ranalletta, Greenville, SC (US); Bernd Krause, Rangendingen (DE)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 994 days.

(21) Appl. No.: 16/631,017

(22) PCT Filed: Jul. 12, 2018

(86) PCT No.: PCT/US2018/041790
§ 371 (c)(1),
(2) Date: Jan. 14, 2020

(87) PCT Pub. No.: WO2019/018195
PCT Pub. Date: Jan. 24, 2019

(65) Prior Publication Data
US 2020/0146931 A1 May 14, 2020

Related U.S. Application Data

(60) Provisional application No. 62/533,515, filed on Jul. 17, 2017.

(51) Int. Cl.
*A61J 1/10* (2006.01)
*A61J 1/20* (2006.01)
(Continued)

(52) U.S. Cl.
CPC .............. *A61J 1/10* (2013.01); *A61J 1/1443* (2013.01); *A61J 1/1475* (2013.01); *A61J 1/2082* (2015.05);
(Continued)

(58) Field of Classification Search
CPC .......... A61J 1/10; A61J 1/1443; A61J 1/1475; A61J 1/2082; A61J 1/2086; A61J 1/2093;
(Continued)

(56) References Cited

U.S. PATENT DOCUMENTS 4,919,860 A * 4/1990 Schindler ............. B01D 71/021
264/102
5,490,848 A 2/1996 Finley et al.
(Continued)

FOREIGN PATENT DOCUMENTS

JP 2004313708 A 11/2004

OTHER PUBLICATIONS

International Search Report for International Application No. PCT/US2018/041790, dated Jul. 16, 2018.
(Continued)

*Primary Examiner* — Ariana Zimbouski
(74) *Attorney, Agent, or Firm* — MARSHALL, GERSTEIN & BORUN LLP

(57) ABSTRACT

A sterile solution product bag for lyophilizing includes a bladder, a first stem having a first stem inlet end and a first stem outlet end. The first stem outlet end is fluidly connected to the bladder and the first stem inlet end is adapted to receive a liquid. A first filter is disposed in-line with the first stem and includes a first filter membrane, a first filter open
(Continued)

end, and a first filter closed end. The first filter closed end is disposed between the first stem inlet end and the first stem outlet end and the first filter open end is disposed in proximity to the first stem inlet end. A second stem having a second stem inlet end fluidly connected to the bladder and a second stem outlet end adapted to receive a vapor. A second filter is disposed within the second stem and includes a filter membrane.

14 Claims, 17 Drawing Sheets

(51) Int. Cl.
  *A61J 1/14* (2023.01)
  *A61L 2/00* (2006.01)
  *F26B 5/06* (2006.01)

(52) U.S. Cl.
  CPC ............ *A61J 1/2086* (2015.05); *A61J 1/2093* (2013.01); *A61L 2/0017* (2013.01); *A61J 1/2024* (2015.05); *A61L 2202/181* (2013.01); *F26B 5/06* (2013.01)

(58) Field of Classification Search
  CPC ...... A61J 1/1468; A61J 1/2037; A61J 1/2024; A61L 1/2024; A61L 2/0017; F26B 5/06; F26B 9/066; B65B 55/12
  See application file for complete search history.

(56) References Cited

U.S. PATENT DOCUMENTS

| | | | | |
|---|---|---|---|---|
| 7,422,726 | B2* | 9/2008 | Hammerstedt | ............ F26B 5/06 426/384 |
| 2009/0113753 | A1* | 5/2009 | Pepper | ................... A61B 50/13 34/92 |
| 2009/0223080 | A1 | 9/2009 | McCarthy et al. | |
| 2015/0158652 | A1 | 6/2015 | Root et al. | |
| 2016/0136051 | A1* | 5/2016 | Lavi | .......................... A61J 1/22 604/407 |

OTHER PUBLICATIONS

Written Opinion for International Application No. PCT/US2018/041790, dated Jul. 16, 2018.

* cited by examiner

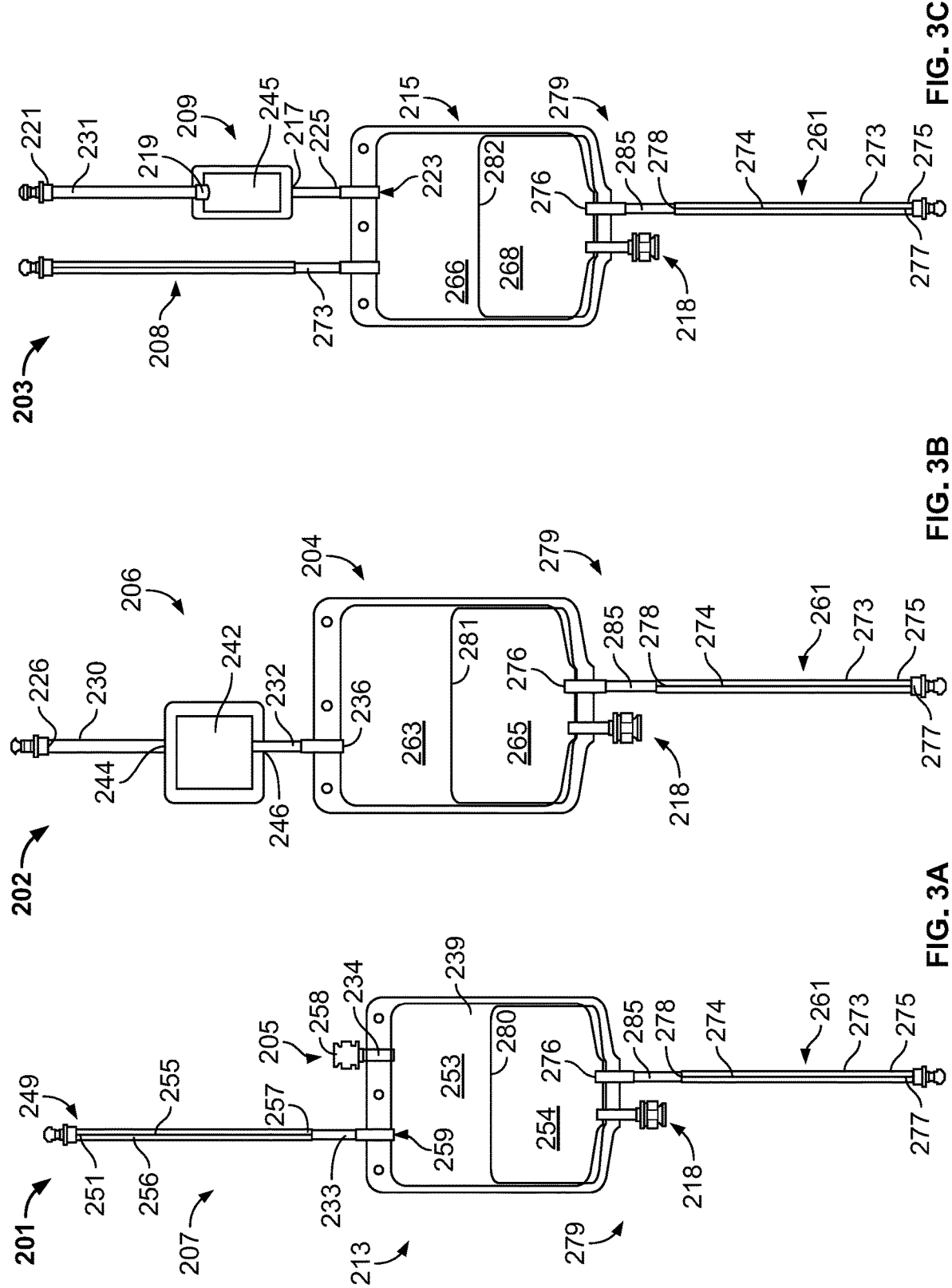

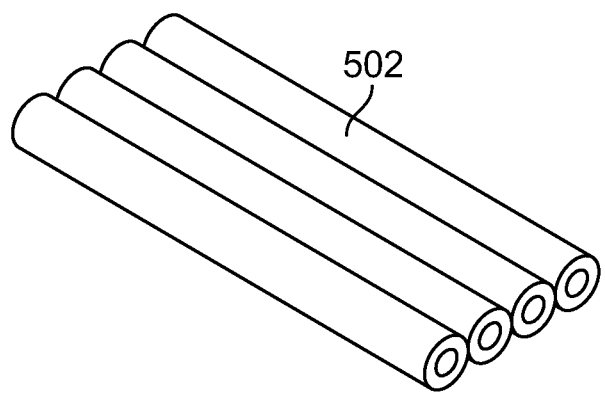
FIG. 13
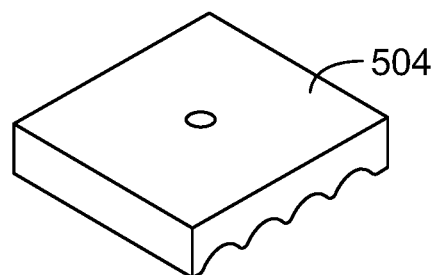
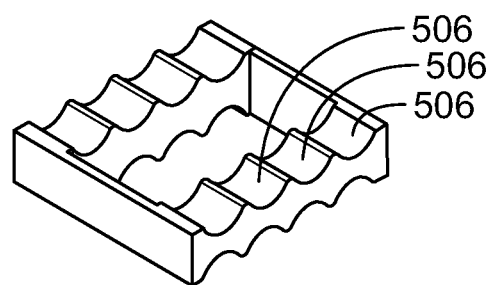
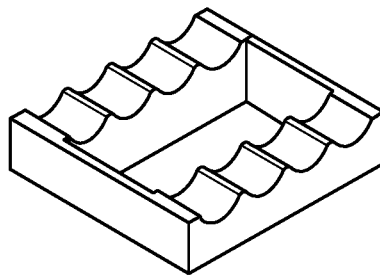
FIG. 14

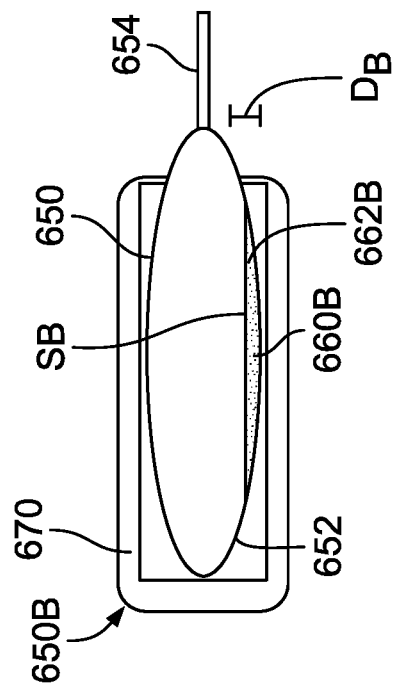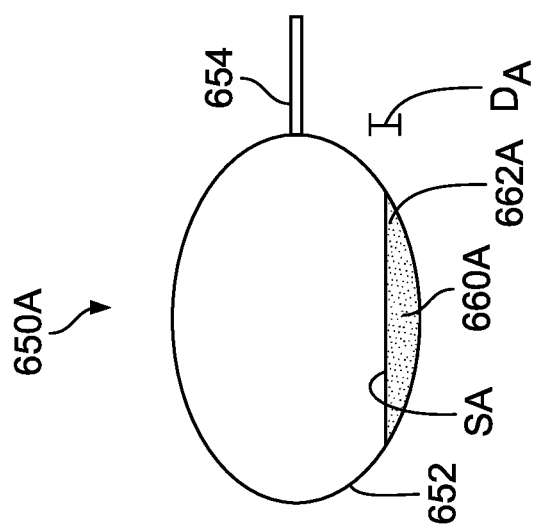
FIG. 26

TERMINAL STERILIZATION FILTRATION CLOSED LYOPHILIZATION IN A CONTAINER

CROSS-REFERENCE TO RELATED APPLICATIONS

This is the United States national phase of PCT/US18/41790, filed Jul. 12, 2018, which claims the priority benefit of U.S. Provisional Application Ser. No. 62/533,515, filed Jul. 17, 2017, the entire contents of each of which are incorporated herein by reference.

FIELD OF THE DISCLOSURE

This disclosure relates to sterile filling of a container, and, in particular, to terminal sterilization filtration and closed lyophilization in a container.

BACKGROUND

The processes required for manufacturing sterile active pharmaceutical ingredients ("APIs") for parenteral administration are strictly controlled to minimize contamination with micro-organisms, endotoxins, and particulate. Quality standards for manufacturing sterile bulk powder APIs require that the APIs are sterile, of correct potency, flowable, and essentially free of particulate, thereby limiting available options of known stabilization techniques during manufacturing. These heat sensitive APIs and biologics are formulated as liquid with pharmaceutically acceptable excipients and then are typically filtered through a sterile filter and downstream processed using aseptic filling and packaging. In addition, some heat sensitive pharmaceuticals and biologics cannot be stabilized in the liquid form and as a result, lyophilization or aseptic crystallization is used to remove the water and stabilize the API in the solid form. In addition, manufacturing drugs in bulk powder-form requires a controlled processing environment and stringent protocols for powder-handling to safely transfer the powder into the final sealed container. Drugs that cannot easily be made into sterile powders, such as biologics, are typically aseptically filtered into a vial followed by lyophilization to create the powder.

Lyophilization, which can also be referred to as freeze-drying, is a dehydration process typically used to preserve a perishable target material or make the target material more convenient for transport. Lyophilization works by freezing the target material and then reducing the surrounding pressure and adding sufficient heat to allow the frozen water in the target material to sublimate directly from a solid to a gas. The gas is then removed from the target material to complete dehydration.

Conventional lyophilization processes are carried out with freeze-drying machines located within laboratories or production facilities, for example, and which define internal chambers for containing the material to be lyophilized. The material to be lyophilized will often be formulated within production facilities and then introduced into the lyophilization chamber in open vessels such as vials, bottles, or other containers. As such, the gas can easily exhaust from the open vessels during the lyophilization process.

In the pharmaceutical industry materials that are lyophilized, however, require more careful handling to prevent contamination. For example, the pharmaceuticals should be contained in a sterile environment while being transported through the laboratories or production facilities before and after lyophilization. The containers which hold or contain the substance to be lyophilized may form a part of a sterile barrier between the substance and the environment, but such containers must be open to enable the gas to exhaust therefrom during lyophilization. The powder resulting from lyophilization may be toxic to handlers even if all stringent conditions of sterility are met, and thus must be handled safely when exposed to the surrounding environment.

For medical containers such as open vials, containing the sterile powder in a sterile environment is maintained using different techniques. For example, prior to going into the lyophilization chamber the vials are filled in a fill room, which must meet certain environmental regulatory standards to avoid risk of contamination. At the end of the lyophilization process for vials, the stoppers are displaced into the vial container so as to seal the mouth. For other containers such as cartridges and syringes, this sealing process may be more difficult or not possible. For the instances where the container cannot be sealed after the lyophilization process is conducted, the lyophilized containers must be maintained in a sterile environment upon exit from the lyophilization chamber until such containers reach a sterile environment for further sealing. Providing a sterile environment immediately adjacent the lyophilization chamber greatly increases the expense and complexity of such production facilities.

To administer these lyophilized products to a patient, the product must be reconstituted with a diluent. Then the reconstituted product must be administered to the patient in the right concentration. Frequently this requires reconstituting within the vial, cartridge or syringe and then injecting the solution into an IV bag filled with further diluent. The reconstitution and injection steps must be done with aseptic technique this increased the time and complexity to place the product in a form appropriate for administration.

SUMMARY

A sterile solution container for lyophilization and method for providing sterile powder concentrate in a sealed container by lyophilization in accordance with the teachings described herein may address the cost limitations and complexity of known processes of lyophilizing and/or administering pharmaceuticals.

In accordance with a first exemplary aspect, a sterile solution product bag for lyophilizing may include a bladder, a first stem having a first stem inlet end and a first stem outlet end. The first stem outlet end may be fluidly connected to the bladder and the first stem inlet end may be adapted to receive a liquid for introduction into the bladder. The product bag may further include a first filter disposed in-line the first stem, the first filter having a first filter membrane, a first filter open end, and a first filter closed end. The first filter closed end may be disposed between the first stem inlet end and the first stem outlet end and the first filter open end may be disposed in proximity to the first stem inlet end. The first filter may be arranged to sterilize the liquid as it passes through the first filter and into the bladder. A second stem may include a second stem inlet end and a second stem outlet end, the second stem inlet end may be fluidly connected to the bladder and adapted to receive a vapor resulting from lyophilization of the liquid in the bladder. A second filter may be disposed in-line the second stem, the second filter having a second filter membrane, a second filter open end, and a second filter closed end. The second filter open end may be disposed in proximity to the second stem inlet end.

In accordance with a second exemplary aspect, a sterile solution container for lyophilization may include a bladder and a stem having an inlet end and an outlet end, where the outlet end may be in fluid communication with the bladder. The container may include a filter membrane disposed between the inlet end and the outlet end of the stem, where the filter membrane may be adapted to filter a liquid solution introduced through the inlet end of the stem to fill the bladder with a sterile liquid solution. The container may include a vapor release member in fluid communication with the bladder and may be adapted to release a vapor from the bladder during lyophilization of the liquid solution while containing a powder product within the bladder.

In accordance with a third exemplary aspect, a method of providing sterile powder in a sealed container by lyophilization may include filling a chamber of a container with a liquid solution through a first filter. The container may include a bladder defining the chamber, a first stem containing the first filter, a second stem containing a second filter, a first port fluidly connecting the first stem to the chamber of the bladder, a second port fluidly connecting the second stem to the chamber of the bladder. The container may be a liquid-filled container when the chamber of the bladder contains the liquid solution. After filling, the method may include sealing the liquid-filled container at the first port, and removing the first stem containing the first filter from the liquid-filled container. The method may include removing liquid of the liquid-filled container by lyophilizing the liquid-filled container, where the liquid may be removed through the second stem. The container may be a powder-filled container when the chamber of the bladder contains powder after lyophilizing.

In accordance with a fourth exemplary aspect, a method of providing sterile powder in a sealed product bag by lyophilization may include filling a product bag with a liquid solution through a filter. The product bag may include a bladder, a stem containing the filter, a port fluidly connecting the stem to the bladder. The product bag may be a liquid-filled product bag when the bladder contains the liquid solution. Further, the method may include removing liquid of the liquid-filled product bag by lyophilizing the liquid solution, during which the liquid is removed from the bladder, thereby resulting in a powdered product in the bladder defining a powder-filled product bag.

In further accordance with any one or more of the foregoing first, second, third, or fourth aspects, a container, product bag, and/or method may further include any one or more of the following preferred forms.

In one form of the product bag, the first filter membrane may have a first surface area and the second filter membrane may have a second surface area, where the first surface area may be less than or equal to the second surface area.

In one form of the product bag, the bladder may include a first chamber and a second chamber, where the first chamber fluidly may be isolated from the second chamber by a seal. The first stem outlet end and the second stem inlet end may be in fluid communication with the first chamber of the bladder.

In one form, the product bag may include a moon seal within the bladder. The moon seal may be adapted to limit powder contained in the bladder from escaping the bladder.

In one form, the product bag may include a third stem having a third stem inlet end and a third stem outlet end, where the third stem outlet end may be fluidly connected to the bladder. A third filter may be disposed in-line with the third stem, and may have a third filter membrane, a third filter open end, and a third filter closed end. The third filter open end may be disposed in proximity to the third stem inlet end.

In one form, the product bag may include a top portion, a bottom portion, and an edge portion connecting the top and bottom portions such that the top, bottom, and edge portions surround the bladder. The bottom portion may include an expandable structure adapted to support the bladder, the first stem, and the second stem in an upright orientation relative to a horizontal surface. The first stem and the second stem may be connected to the bladder at the top portion.

In one form, the product bag may include a wall defining the bladder that includes a porous material having a pore size range allowing sufficient permeability such that gas leaves the bladder at a desired lyophilization rate. The pore size may be in a range of approximately 0.5 nm to approximately 230 nm. The pores may be adapted to expand during lyophilization to permit vapor formed in the bladder to pass through the pores.

In one form of the product bag, at least one of the first filter membrane and the second filter membrane may have a nominal pore size in a range of approximately 0.1 μm to approximately 0.5 μm, wherein the at least one filter membrane may include a walled hollow fiber with pores residing in the wall.

In one form of the product bag, at least one of the first filter and the second filter may include a plurality of filter membranes.

In one form of the product bag, at least one of the first filter and the second filter may include at least one U-shaped hollow fiber filter membrane.

In one form of the container, the vapor release member may include the stem and the filter membrane.

In one form of the container, the vapor release member may include a one-way valve adapted to release vapor during lyophilization.

In one form of the container, the vapor release member may include a second stem having a second stem inlet end and a second stem outlet end, where the second stem inlet end may be fluidly connected to the bladder. A second filter membrane may be disposed in-line with the second stem and between the second stem inlet end and the second stem outlet end. The second filter membrane may include an opening disposed in proximity to the second stem inlet end.

In one form of the container, the vapor release member may include a porous wall surrounding the bladder. The porous wall may have a pore size in a range of approximately 0.5 nm to approximately 230 nm and yet be capable of passing a bacterial challenge to retain a minimum of 107 cfu/cm$^2$ of $B.\ diminuta$. The pores may be adapted to expand during lyophilization to permit vapor formed in the bladder to pass through the pores.

In one form of the container, the bladder may include a first chamber and a second chamber, where the first chamber may be fluidly isolated from the second chamber by a seal. The outlet end of the stem and vapor release member may be in fluid communication with the first chamber of the bladder.

In one form, the container may include a diluent stem having a diluent inlet end and a diluent outlet end, where the diluent outlet end may be in fluid communication with the bladder. A diluent filter membrane may be disposed between the diluent inlet end and the diluent outlet end.

In one form, the container may include a top portion, a bottom portion, and an edge portion connecting the top and bottom portions such that the top, bottom, and edge portions surround the bladder. The bottom portion may include an expandable structure adapted to support the bladder, the stem, and the vapor release member in an upright orientation relative to a horizontal surface. The stem and the vapor release member may be connected to the bladder at the top portion.

In one form, the container may include a moon seal disposed within the bladder, where the moon seal may be adapted to limit powder contained in the bladder from escaping from the bladder.

In one form, the container may include a plurality of filter membranes.

In one form, the method may include, after removing liquid, sealing the powder-filled container at the second port, and removing the second stem containing the second filter.

In one form, the method may include, after removing the first stem, performing an integrity test on the first filter, and correlating an integrity of the liquid solution of the liquid-filled container to an integrity of the first filter based on an outcome of the integrity test.

In one form, the method may include, after removing the second stem, performing an integrity test on the second filter, and correlating an integrity of the sterile powder of the powder-filled container to an integrity of the second filter based on an outcome of the integrity test.

In one form of the method, removing liquid may include freeze-drying the liquid-filled container in a pressurized lyophilization chamber.

In one form, the method may include inserting the liquid-filled container within a rigid container prior to removing the liquid from the container.

In one form, the method may include filling a second chamber of the bladder with a diluent through a third filter disposed within a third stem. A third port may fluidly connect the third stem with the second chamber, where the second chamber may be fluidly sealed from the chamber containing the powder. The second chamber may be a liquid-filled second chamber when the second chamber contains the diluent.

In one form, the method may include sealing the liquid-filled second chamber at the third port and removing the third stem from the container after filling the second chamber.

In one form, the method may include, after filling, sealing the liquid-filled product bag at the port, and removing the stem containing the filter from the liquid-filled product bag.

In one form, the method may include, after removing liquid, sealing the powder-filled product bag at a second port, where the second port may fluidly connect the vapor release member to the bladder during lyophilization.

In one form, the method may include removing a second stem containing a second filter from the second port, wherein the vapor release member may include the second stem and the second filter.

In one form, the method may include filling the bladder with a diluent through a diluent filter contained in a diluent stem, where the diluent stem may be fluidly connected to the bladder and contains the diluent filter.

In one form of the method, filling the bladder with a diluent may include filling a second chamber of the bladder with the diluent, where the second chamber may be fluidly sealed from a first chamber containing the powder. The second chamber may be a diluent-filled second chamber when the second chamber contains the diluent.

In one form, the method may include sealing the diluent-filled second chamber at a diluent port and removing the diluent stem from the product bag after sealing the second port.

In one form, removing liquid from the bladder may include removing liquid through a vapor release member comprising one of (a) a one-way valve, (b) the stem and the filter, (c) a second stem and a second filter, or (d) a porous wall of the bladder that allows vapor release.

BRIEF DESCRIPTION OF THE DRAWINGS

While the specification concludes with claims particularly pointing out and distinctly claiming the subject matter that is regarded as the present disclosure, it is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIG. 3A is a front view of a multi-chamber product bag with a fourth exemplary filtration system in accordance with the teachings of the present disclosure;

FIG. 3B is a front view of a multi-chamber product bag with a fifth exemplary filtration system in accordance with the teachings of the present disclosure;

FIG. 3C is a front view of a multi-chamber product bag with a sixth exemplary filtration system in accordance with the teachings of the present disclosure;

FIG. 13 is a front view of a plurality of hollow fiber membranes secured side by side that may be representative of any of the filter membranes of FIGS. 1-4A;

FIG. 14 is an isometric view of the securement device used for the plurality of hollow fiber membranes depicted in FIG. 13;

FIG. 26 illustrates certain effects of lyophilization on two identical product bags, shown alone and within a container, in accordance with the teachings of the present disclosure.

DETAILED DESCRIPTION

Figure 1:
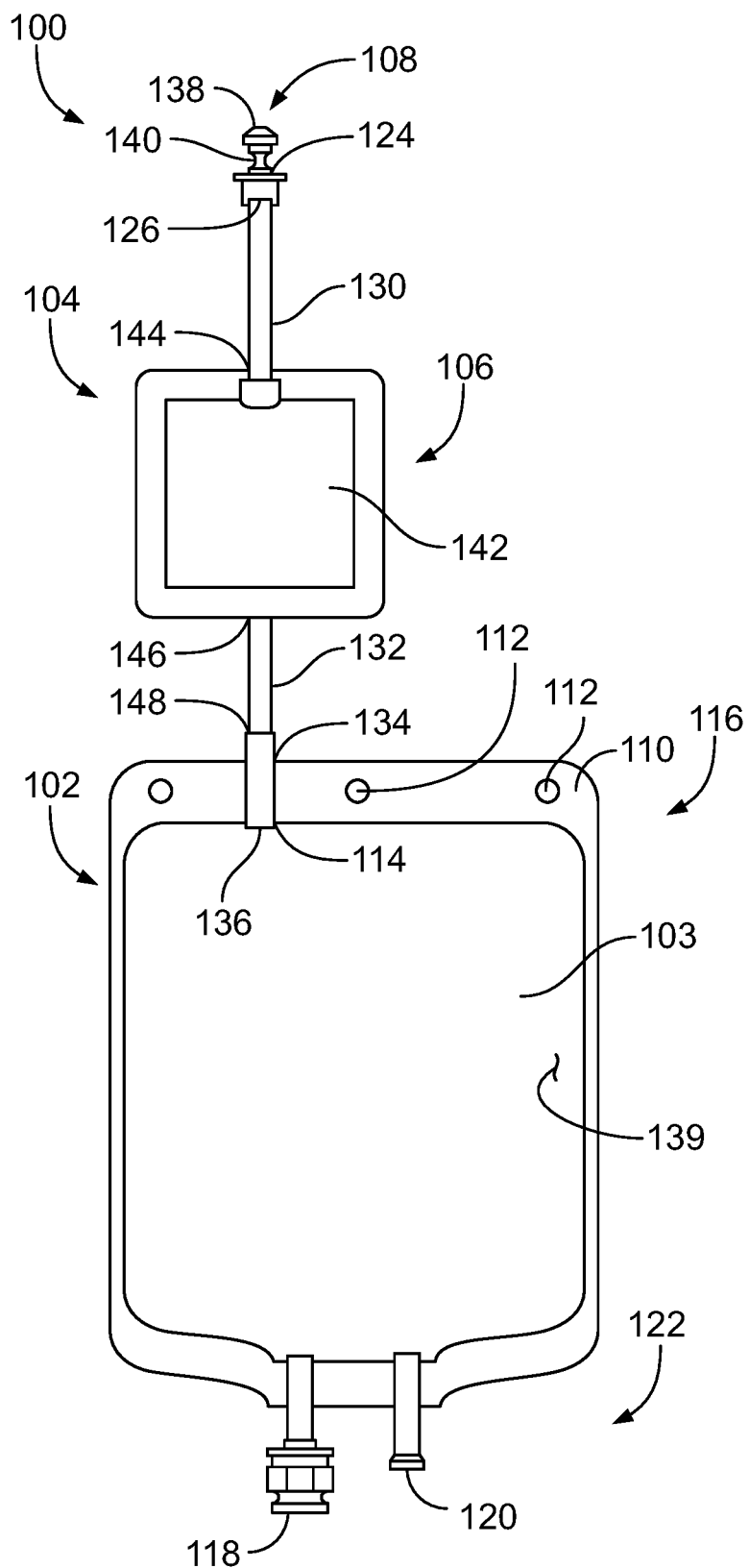
FIG. 1 is a front view of a product bag having a first exemplary filtration system in accordance with the teachings of the present disclosure.

A sterile container, such as a sterile solution product bag, and method of providing a sterile solution container with a sterile powder concentrate by lyophilization provides a sterilization process for pharmaceuticals, such as biologics, that are not stable as a liquid and/or are heat sensitive. The sterile container and method using the sterile container incorporates terminal sterilization filtration and local solution manufacturing technology ("LSMT") to sterile filter a liquid solution in a closed container, and to remove sublimed water vapor from the container without opening, and therefore possibly contaminating, the container to the surrounding environment. As a result, a sterile, powder concentrate is sealed within the container.

At different phases of the disclosed process, the LSMT sterile filtration system may be tested for quality assurance. As used herein, the term "filtration system" may encompass the combined assemblies (LSMT or otherwise), members, and mechanisms involved in introducing fluids into, and removing fluids from, a terminally-sterilized container, such as a plastic product bag. The filtration system of each container embodiment may include one or more filter assemblies (including a diluent filter assembly), vapor release member, and/or other mechanism that either sterile filter a liquid solution and/or permit vapor release. The term "filter assembly," as used herein, may define any filter and stem arrangement, and a "vapor release member," as used herein, may define any mechanism which permits vapor to be removed from the closed container. In some examples, a vapor release member may include a filter assembly.

Two exemplary types of containers are configured to meet the foregoing. A first type or configuration is described primarily with reference to FIGS. 1-2B and 22, and includes a single-chamber product bag. Generally, the product bag is provided with an empty chamber that is pre-sterilized by gamma or terminal sterilization, for example. A fluid is introduced, such as a liquid biologic, on-demand to the empty chamber through a sterilization filtration system of the bag, so that the fluid is sterilized and resident by itself in the previously empty chamber. Subsequently, the product bag containing the sterile solution may be lyophilized. During lyophilization, the water of the sterile solution is frozen and placed under a vacuum, allowing ice to change directly from solid to gas in the product bag. Through the filtration system of the product bag, the vapor is removed, leaving a powder concentrate sealed within the chamber. A sterile diluent may later be introduced to the chamber containing the sterile powder concentrate for reconstitution prior to being administered to a patient.

The second exemplary type or configuration of a sterile product bag is described primarily with reference to FIGS. 3A-4B, 23, and 24 and includes a sterile multi-chamber product bag having at least two chamber portions separated by, for example, a "peelable seal." With this configuration, a first chamber is sterile filled with a fluid solution and lyophilized in the same manner as the single-chamber container to produce a sterile powder concentrate sealed in the first chamber. A diluent may be introduced to the second chamber portion, and the contents of each chamber can be mixed by breaking the peeleable seal or film separating the chambers. For example, hydraulic pressures may be created by squeezing the product bag to break the peelable seal and mix the contents of the two chamber portions. An example lyophilization system and additional embodiments of the product bags are described with reference to FIGS. 21, 25 and 26. Each of these embodiments will now be described in more detail.

Single-Chamber Container

Turning to the first type of sterile container, in FIG. 1 an empty, sterile product bag 100 and filtration system 106 is illustrated. The filtration system 106 includes a vapor release member that includes, or is integrated with, a filter assembly. The vapor release member 106 is in fluid communication with a pre-sterilized interior chamber 103 of a bladder 102 and includes a stem 104 and a filter 142 disposed in-line with the stem 104. The chamber 103 of the bladder 102 is fluidly connected to the stem 104 at a bladder opening 114 at a first end 116 of the bladder 102. In particular, the bladder 102 is a fillable pouch with a standard volume capacity defined by a bladder wall 139. At least partially surrounding a perimeter of the fillable pouch is a sealed perimeter 110 having a plurality of apertures 112 configured to receive mounting hang-pins during filling, lyophilization, administration, and/or storage. The product bag 100 is formed from a flexible sheet of plastic material, such as, for example, a clarity 3PV or other suitable material, and the bladder 102 may be formed from two sheets of film that are heat sealed along their edges to define the perimeter seal 110. In another embodiment, the bag 100 can be formed from a web of film folded over and sealed along three sides. An administration port 118 and a vial adaptor 120 are disposed at a second end 122 of the bladder 102. Other ports can be included as desired.

The stem 104 of the vapor release member 106 is a hollow narrow tube, having a stem inlet end 124 and a stem outlet end 136, where the stem inlet end 124 is adapted to receive a solution and the stem outlet end 136 is fluidly connected to the opening 114 of the bladder 102. The stem 104 includes a tapered head 126 defining the stem inlet end 124, a first stem part 130 connected to the tapered head 126, a second part 132, and a duct 134 defining the stem outlet end 136. The sterile closure cap 108 has a hemispherical shaped knob 138 attached to a neck that sealably covers the stem inlet end 124 to maintain sterility until necessary to remove the knob 138 for filling. The tapered head 126 may be a female fitting adapted for sealing and engaging a Luer fitting of a fluid supply line during filling, for example. The filter 106 in this version has a flat sheet filter membrane 142 disposed in-line within the stem 104 between the first and second parts 130 and 132 of the stem 104. The filter membrane 142 includes a filter open end 144 and a filter closed end 146, where the filter closed end 146 is disposed between the stem inlet end 124 and the stem outlet end 136, and the filter open end 144 is disposed in proximity to the stem inlet end 124. The second part 132 of the stem 104 defined as the area of the stem 104 between the filter closed end 146 and an inlet 148 of the duct 134 may be identified as a "seal and cut area." The "seal and cut area" facilitates separation of that portion of the stem 104 containing the filter membrane 142. Because the "seal and cut area" 132 exists, the filter membrane 142 can be separated intact. As described further below, the "seal and cut area" 132 can advantageously facilitate an integrity test procedure on the filter membrane 142.

In the illustrated example of FIG. 1, the vapor release member 106 is involved with both sterile filling the product bag with solution and releasing and/or removing the vapor. So configured, a liquid pharmaceutical may enter the stem inlet end 124 of the stem 104 and pass through the head 126 and into the first part 130 toward the filter open end 144 of the filter 142. The solution then passes through the filter membrane 142 and out a filter outlet, such as a plurality of pores, near the filter closed end 146, and into the second part 132 of the stem 104. The port or duct 134 carries the filtered solution from the second part 132 to the opening 114 of the bladder 102, which leads to the empty sterile chamber 103. The plurality of pores disposed on an outer wall of the filter membrane 142 may be sized to sufficiently sterilize the solution before the solution enters the chamber 103 of the bladder 102. The filter membrane 142 of the vapor release member 106 is also configured to permit the vapor to pass through the pores of the filter membrane 142 during lyophilization while the concentrated powder remains within the chamber 103.

To enhance the filtering capabilities, the filter membrane 142 may be supplemented with active filter enhancement materials, for example, filters that would not only terminally sterilize the products while being filled, but would also actively remove components that could be detrimental to the formulation of the concentrate, e.g., oxygen, impurities, degradants, or even particular microbes. Active filter enhancement materials may include incorporation or attachment of ascorbic acid, iron-based systems, catechol, enzyme-based systems, chitosan, antibodies, etc., onto or into the polymer used to create the filter (e.g., polysulfone, polyvinylpyrrolidone, polyethyleneimine, polyamide, etc.). Filter membranes 142 are constructed from materials that resist deformation during large temperature changes, such as those that occur during lyophilization (e.g., −70 C to 50 C), which may also result in decreased microbial filter retention. Non-limiting examples of acceptable filter membranes for the filter membranes of the present disclosure are disclosed in U.S. Patent Publication No. 2012/0074064 A1 and PCT Publication No. PCT/EP2015/068004, the entire contents of which are incorporated herein by reference.

In other example filtration systems, the vapor release member 106 may be constructed separately from a filter assembly used for sterile-filling the product bag 100 (FIGS. 2A-3A, 3C). In some cases, the vapor release member 106 may not include a filter membrane 142. For example, the vapor release member 106 may be a permeable bladder, a one-way valve (FIG. 3A), a filter assembly with a walled hollow fiber membrane (FIG. 2A), a second LSMT filter assembly (FIGS. 2A, 2B, 3C), or other pathway to permit vapor removal from the chamber of the bladder. In any of these embodiments, the bladder 102 could also serve as a supplemental or additional vapor release member. For example, the bladder wall 139 may be a micro-porous and/or permeable material that may increase vapor flow from the bladder 102 during lyophilization. The pores of a micro-porous bag may expand when lyophilized to a size large enough for vapor to pass through. The bladder wall 139 that defines the bladder 102 of the product bag 100 may be a micro or nano porous material having a pore size in a range of approximately 0.5 nm to approximately 230 nm, and preferable 1.0 nm to 220 nm, where the pores are adapted to expand to a suitable size during lyophilization to permit vapor to pass through and yet be capable of passing a bacterial challenge to retain a minimum of 107 cfu/cm$^2$ of *B. diminuta*. A suitable pore size may be in a range allowing sufficient permeability such that gas leaves the bladder 102 at a desired lyophilization rate. When the lyophilization is complete, and the product bag 100 is brought back to initial conditions, returning the pores to their original size (or close to their original size), and thereby sealing the powder concentrate within the chamber 103. The bladder 102 may be a permeable plastic material such as Silicone, Urethane, Polycarbonate, PFA (Perflouroalkoxy alkane), and PVF (Polyvinyl Fluoride).

Figure 2A:
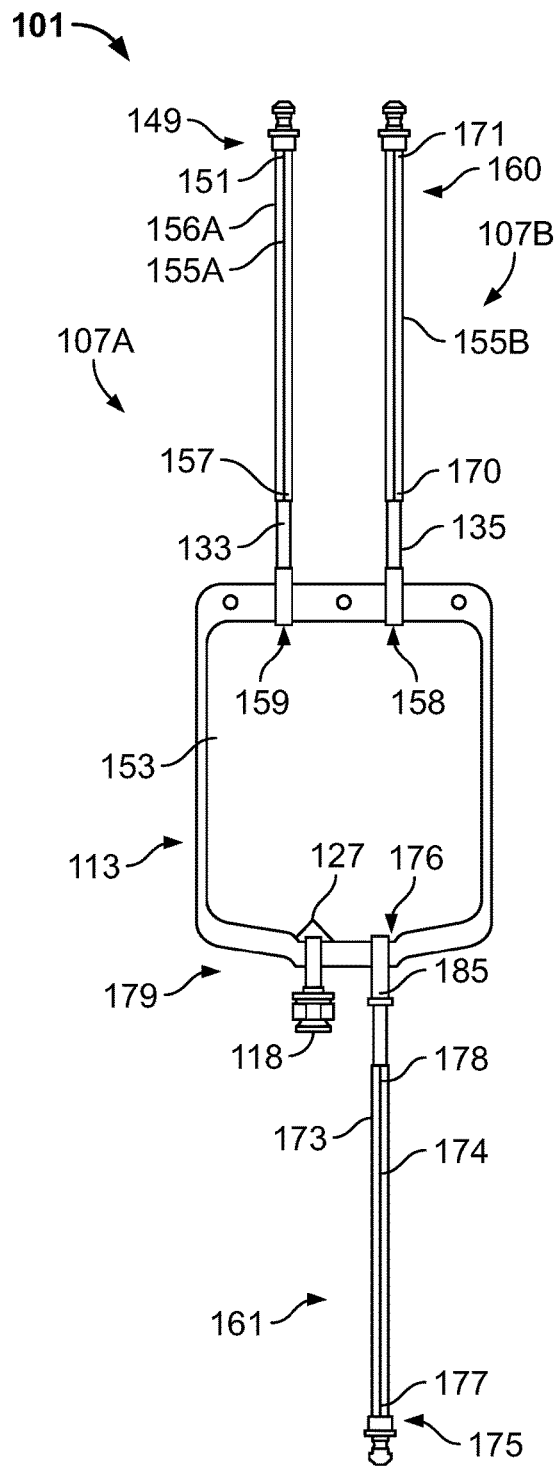
FIG. 2A is a front view of a product bag having a second exemplary filtration system in accordance with the teachings of the present disclosure.
Figure 2B:
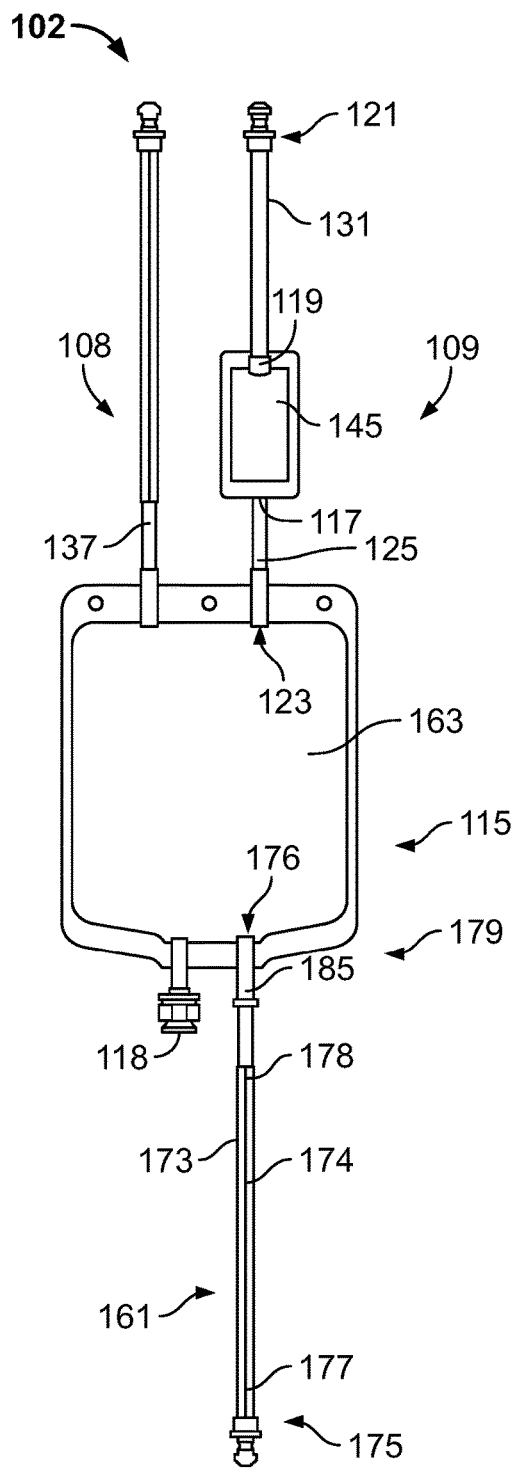
FIG. 2B is a front view of a product bag having a third exemplary filtration system in accordance with the teachings of the present disclosure.
Figure 5:
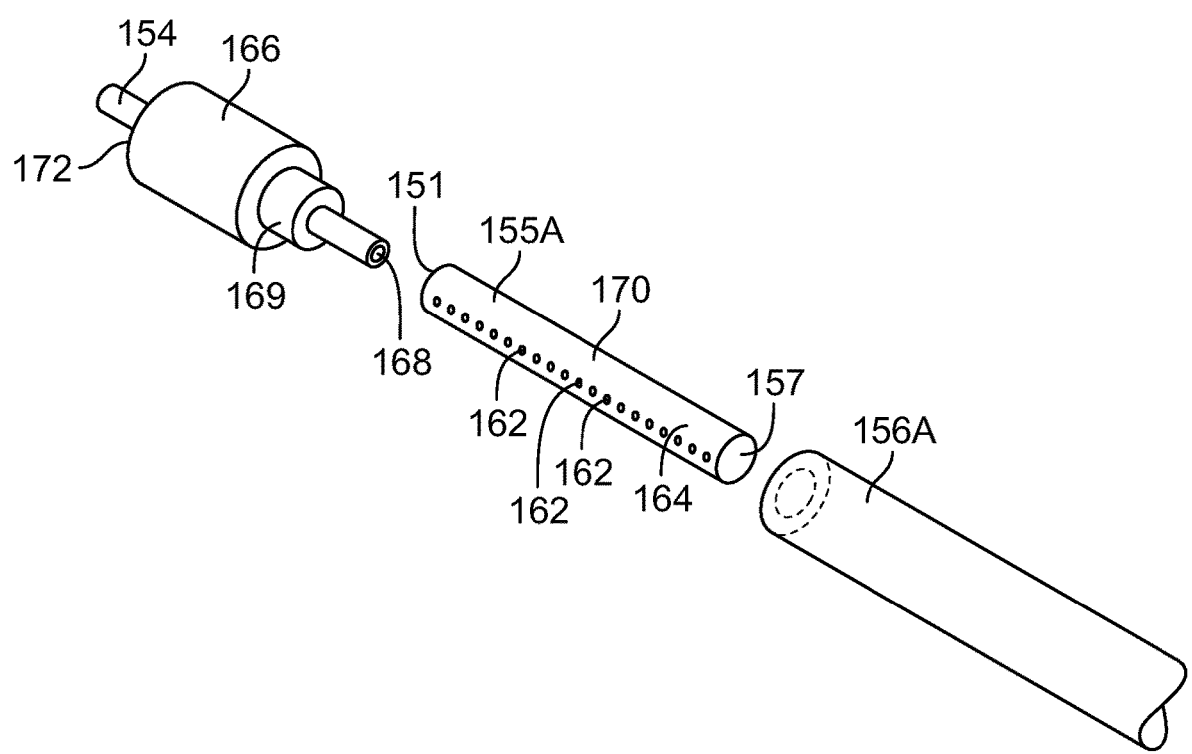
FIG. 5 is an expanded isometric view of a filter assembly representative of any of the filter assemblies of FIGS. 1-4A.
Figure 6:
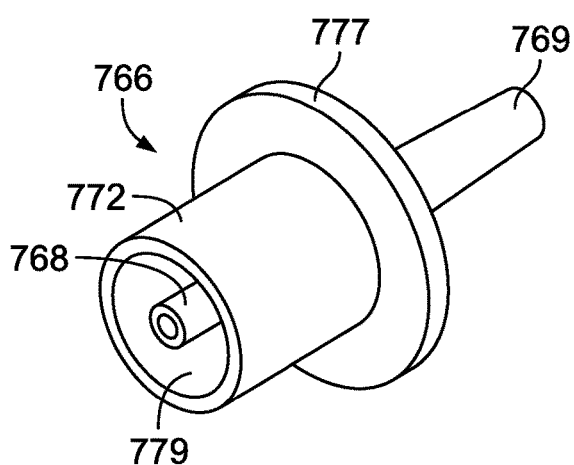
FIG. 6 is a perspective view of an alternative connector for use with a filter and stem such as the filter assembly of FIG. 5.
Figure 7:
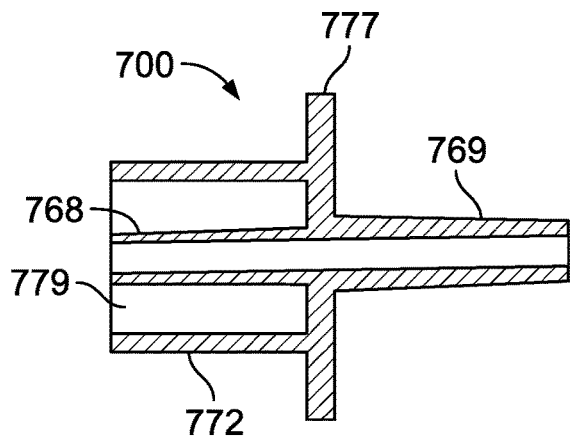
FIG. 7 is a side cross-sectional view of the connector of FIG. 6.
Figure 8:
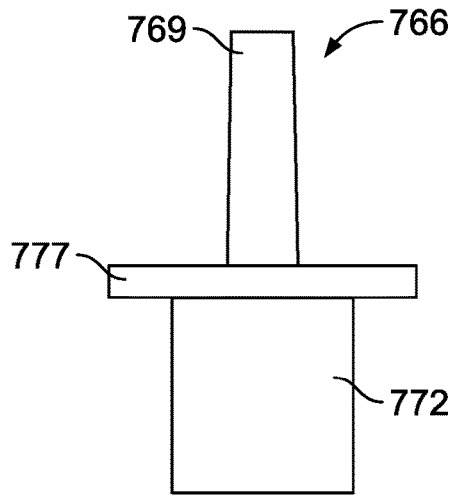
FIG. 8 is a side view of the connector of FIG. 6.
Figure 9:
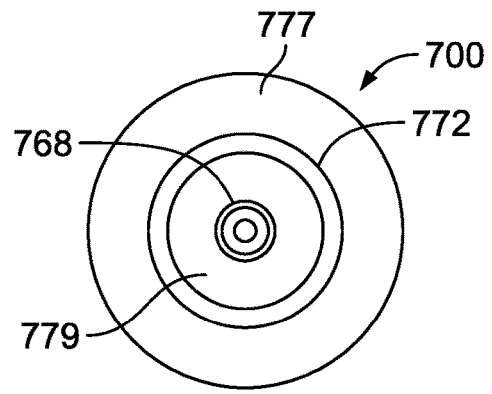
FIG. 9 is a bottom view of the connector of FIG. 8.
Figure 10:
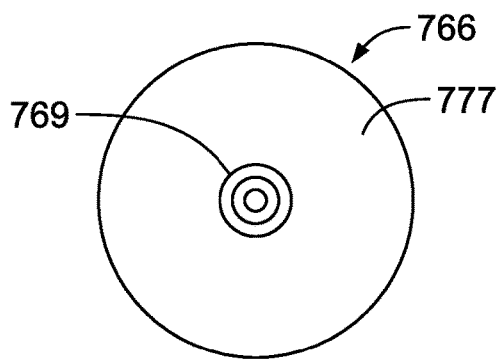
FIG. 10 is a top view of the connector of FIG. 8.

FIGS. 2A and 2B illustrate single-chamber sterile product bags 101 and 102 with different filtration systems. In FIG. 2A, the product bag 101 includes a first filter assembly 107A, also generally referred herein as the "first filter," with a first stem 156A having a first stem inlet end 149 and a first stem outlet end 159. The first stem outlet end 159 fluidly connects to a chamber 153 of a bladder 113, and the first stem inlet end 149 is adapted to receive a solution. The first filter 107A includes a filter membrane 155A disposed in-line and within (i.e., at least partially or entirely inside of) the first stem 156A. The first stem 156A, which may be tapered or cylindrical, may not provide a separate inlet and outlet connection ports for the filter 155A as illustrated in the product bag 100 of FIG. 1. Instead, and as also shown in FIG. 5, the filter membrane 155A can be a walled hollow fiber membrane with a plurality of pores residing in the wall. The filter 155A includes a first filter open end 151 and a first filter closed end 157. The first filter closed end 157 is disposed between the first stem inlet end 149 and the first stem outlet end 159, and the first filter open end 151 is disposed in proximity to the first stem inlet end 149. The filter assembly 107A can include any of the filters, filter membranes, and filtration devices described below with respect to FIGS. 5-20.

Referring to FIG. 5, the first filter closed end 157 may be capped or sealed with a heat seal, an adhesive, or some other means. A plurality of pores 162 disposed along the surface 164 of the filter membrane 155A allow a pharmaceutical fluid that enters the filter 107A at the first filter open end 151 to exit the filter membrane 155A. In one version, the stem 156A surrounds the filter membrane 155A in a generally concentric configuration so filtered pharmaceutical fluid exiting the filter membrane 155A is contained within the stem 156A and ultimately passes into the chamber 153 of the bladder 113. Again, like in FIG. 1, the product bag 101 in FIG. 2A includes a "seal and cut area" 133 below the filter 155A and above a bladder 153, wherein the "seal and cut area" 133 facilitates separation of that portion of the stem 156A containing the filter membrane 155A. Because the "seal and cut area" 133 exists, the filter membrane 155A can be separated intact. As described further below, the "seal and cut area" 133 can advantageously facilitate an integrity test procedure on the filter 155A.

The product bag 101 of FIG. 2A also includes a vapor release member, which in this case, is a second filter assembly 107B, referred herein as the "second filter." The second filter 107B includes a second stem 156B having a second stem inlet end 158 and a second stem outlet end 160, where the second stem inlet end 158 is fluidly connected to the chamber 153 of the bladder 113 and is adapted to receive a vapor. A second filter membrane 155B is disposed in-line with the second stem 156B and includes a second filter open end 170 and a second filter closed end 171, where the second filter open end 170 is disposed in proximity to the second stem inlet end 158. The second filter membrane 155B may be similar to the first filter membrane 155A in that the second filter membrane 155B includes a plurality of pores disposed along the surface of the membrane 155B. The pores of the second filter membrane 155B may be different in size to allow a vapor formed in the bladder 113 during lyophilization to enter the second filter 107B at the second filter open end 170 and exit through the pores of the filter membrane 155B. The second stem 156B surrounds the second filter membrane 155B in a generally concentric configuration so filtered vapor exiting the filter membrane 155B is contained within the second stem 156B until it ultimately passes out of the second stem outlet end 160. The second filter assembly 107B may include a moon seal 127 disposed within the bladder and between the chamber 153 and the administration port 118 to keep the powder contained within the chamber 153 during lyophilization.

The first and second filter membranes 155A and 155B of the first and second filters 107A and 107B, respectively, may have different pore sizes and/or different surface areas. For example, a first surface area of the first filter membrane 155A may be less than or equal to a second surface area of the second membrane 155B. In a preferred embodiment, the filter membrane 155B of the second filter 107B that receives the vapor from the product bag 101 has an increased surface area to enhance product flow, and therefore vapor removal, during lyophilization. The vapor release member, or second filter 107B, may include one or more filters, including a flat filter, stacked filters, and other structures that increase the filtration surface area to raise the rate of lyophilization.

In FIG. 2B, the sterile product bag 102 includes a first filter assembly 108, which is substantially similar to the first filter 107A of FIG. 2A, and a vapor release member 109. The vapor release member 109 is a second filter assembly that operates in a similar manner as the second filter 107B of FIG. 2A. In this embodiment, the second filter 109 includes a flat filter membrane 145, such as the filter membrane 142 of the product bag 100 in FIG. 1. For both product bags 100 and 102, the vapor release members 106 and 109 may also serve to sterile fill the bladder with a diluent for drug reconstitution.

Both product bags 101 and 102 of FIGS. 2A and 2B include a third filter assembly 161, which is in fluid communication with their respective bladders 113 and 115 at a bottom ends 179 of the product bags 101 and 102. The third filter assembly 161, also referred herein as the "diluent filter," is similar to the filter assemblies 107A of FIGS. 2A and 5 and 108 of FIG. 2B, and may be any LSMT filter. The third filter 161 includes a third stem 173, a third stem inlet end 175, and a third stem outlet end 176, where the third stem outlet end 176 is fluidly connected to each chamber 153 and 163 of the bladder 113 and 115. A third filter 174 is disposed in-line or within the third stem 173, and includes a third filter membrane 174, a third filter open end 177, and a third filter closed end 178. The third filter open end 177 is disposed in proximity to the third stem inlet end 175. The product bags 101 and 102 may be manufactured with or without the third filter 161 to introduce a diluent to a powder concentrate contained in the chambers 153 and 163 after lyophilization is complete. The diluent may be filtered through the filter membrane 174 and may enter the chamber 153 and 163 via the third stem outlet end 176. The product bag 100 of FIG. 1 may include a third filter assembly 161 in place of the vial adapter 120.

Turning back to FIG. 1, the second part 132 of the stem 104 is identified as the "seal and cut area." Similarly, each stem of the filters 107A, 107B, 108, 109, and 161 of FIGS. 2A and 2B also includes a seal and cut area 133, 135, 137, 125, and 185, respectively. The phrase "seal and cut area" pertains to the manner in which the product bags 100, 101, and 102 are sealed and cut after the filter and stem are no longer needed. Sealing of the "seal and cut area" can be achieved with a heat sealer or any other device, including, for example, clamping a clamp onto the "seal and cut area." Once the stem is sealed, the stem is cut at a location above the seal but below the filter membrane. Cutting may be achieved with a knife or any other device. The stem of the product bag, for example, provides an isolated fluid connection between the stem inlet end and the chamber of the bladder, such that once the solution is filtered through the filter membrane, the filtered solution passes directly into the sterilized environment of the empty chamber of the bladder. Hence, after the bladder receives the sterilized solution and the stem is sealed and cut, the fluid in the bladder remains sterile until the bladder is punctured or compromised. This, of course, assumes that the filter was uncompromised prior to filling and performed as desired. When the vapor release member also sterile fills the product bag (FIG. 1), the stem may be sealed and cut after both the solution is introduced into the chamber and after lyophilization is complete.

To ensure that the filters 106, 107A, 107B, 108, 109, and 161 performed properly, a filter integrity test can be performed on the filters 106, 107A, 107B, 108, 109, and 161. A filter integrity test is facilitated by the arrangement of the "seal and cut area" of the stems, which allow for the filter membrane to be separated intact from the remainder of the now-sealed product bag. For example, after the stem 104 and filter membrane 155A are separated from the product bag 100 of FIG. 1, a filter testing device (not shown) may be pre-programmed or controlled to perform a filter integrity test on the filter 106. Examples of filter integrity tests might include a bubble point test, a pressure degradation test, a water intrusion test, a water flow test, or any suitable test known in the art. A pressure degradation test is a method for testing the quality of a filter either before or after the filter has been used. In the preferred embodiment, the filter 106 is tested after the solution passes through the filter membrane 155A and into the bladder 102 and after lyophilization is complete. To perform the filter integrity test using a pressure degradation test procedure, a test head (not shown) engages the stem 104 and applies an air pressure of a predetermined value to the inlet 124 and filter membrane 155A. In one embodiment, the predetermined value is the pressure where gas cannot permeate the filter membrane 155A of an acceptable filter. A pressure sensor, or other method of measuring the integrity of the filter, is located within the test head and measures the pressure decay or diffusion rate through the filter membrane 155A. The results from the integrity test are assessed to determine the quality of the filter 106, and therefore the quality of the powder lyophilized from the solution that previously passed through the filter 106 and into the product bag 100. If the pressure sensor measures a decay or a unexpected rate of decay, then the filter fails the test and it can be determined that the powder in the product bag is unsatisfactory. Alternatively in a bubble point test, the test head gradually increases the pressure applied to the filter 106, and the increase in pressure is measured in parallel with the diffusion rate of the gas through the filter membrane 155A. Any disproportionate increase in diffusion rate in relation to the applied pressure may indicate a hole or other structural flaw in the filter membrane 155A, and the filter 106 would fail the integrity test. A separate integrity test may be performed before lyophilization to determine the sterility of the solution in the product bag.

Thus, it can be appreciated that the disclosed arrangement of the "seal and cut area" of the product bags disclosed herein advantageously facilitates the filter integrity test, and a determination that the solution and/or powder concentrate in the product bag is either sterile or has the potential of being compromised may be made with a high degree of certainty.

Multi-Chamber Container

Thus far, only sterile product bags 100, 101, and 102 of FIGS. 1-2B having a single chamber 103, 153, and 163 have been discussed. But the benefits of the present disclosure can also be realized in sterile product bags with more than a single chamber. As an example, one conventional two-chamber product bag that can benefit from the technologies of the present application is disclosed in U.S. Pat. No. 5,577,369, entitled METHOD OF MAKING AND FILLING A MULTI-CHAMBER CONTAINER, the entire contents of which are incorporated herein by reference.

FIG. 3A illustrates a multi-chamber product bag 201 with a bladder 213 defining a first or upper chamber 253 fluidly sealed from a second or lower chamber 254 by a seal or film 280. The filtration system of the bag 201 includes a filter assembly 207, a vapor release member 205, and a diluent filter assembly 261. The filter assembly 207 includes a stem 256 having an inlet end 249 and an outlet end 259 in fluid communication with the bladder 213. In particular, the outlet end 259 is in fluid communication with the upper chamber 253 of the bladder 213. Similar to the filter assemblies previously described, the filter assembly 207 includes a filter membrane 255 disposed between the inlet end 249 and the outlet end 259 of the stem 256, and is adapted to filter a liquid solution. The filter membrane 255 may be a walled hollow fiber membrane having an open filter end 251 and a closed filter end 257. The vapor release member 205 is in fluid communication with the first chamber 253 of the bladder 213 and provides a one-way flow path 234 for removing vapor formed in the bladder 213 during lyophilization. The vapor release member 205 is configured to release the vapor while maintaining a sterile powder concentrate disposed within the first chamber 253 of the bladder 213. To facilitate lyophilizing the solution in the first chamber 253, the seal 280 separating the first and second chambers 253 and 254 may be a permeable film seal that would allow some water mass to transfer directly through the film during lyophilization.

For this product bag 201, the vapor release member 205 is a one-way valve with a sealed outlet 258 configured to limit any powder formed in the bladder 213 from entering the inlet or pathway 234 of the vapor release member 205 during lyophilization. So configured, the vapor formed in the upper chamber 253 may pass through the inlet 234 of the vapor release member 205 until the sealed outlet 258 opens to release the vapor. The one-way valve 205 may be constructed so that fluid may flow in one direction from the bladder 213 to the surrounding environment (e.g. lyophilization chamber) without exposing the chamber 253 of the bladder 213 to contamination. The inlet 234 of the vapor release member 205 is in fluid communication with the chamber 253, but does not fluidly connect the outlet 258 to the chamber 253 until vapor is formed during lyophilization. The outlet 258 of the vapor release member 205 is configured to close when all the vapor is removed from the chamber 253. In other embodiments, the vapor release 205 member may include a filter assembly, such as any one of the filter assemblies 106 of FIG. 1, 107B of FIG. 2A, and 109 of FIG. 2B. In yet another embodiment, a bladder wall 239 defining the chamber 253 may be a porous material capable of expanding during the lyophilization process to facilitate vapor removal. In yet another embodiment, the vapor release member 205 may be a combination of any of these mechanisms.

The product bag 201 of FIG. 3A includes a diluent filter assembly 261 fluidly coupled to the second chamber 254 of the product bag 201. The diluent filter assembly 261, also referred herein as the diluent filter, is similar to the third filter assembly 161 of FIGS. 2A and 2B. The diluent filter assembly 261 is attached to the product bag 201 at a bottom end 279 of the product bag 201 and includes a diluent stem 273, a diluent inlet end 275, and a diluent outlet end 276, where the diluent outlet end 276 is fluidly connected to the chamber 254 of the bladder 213. A diluent filter membrane 274 is disposed in-line or within the diluent stem 273, and includes a diluent filter open end 277 and a diluent filter closed end 278. The diluent filter open end 277 is disposed in proximity to the diluent inlet end 275. The diluent filter 261 is provided to the product bag 201 to introduce a sterile diluent to the empty sterile chamber 254 after a powder concentrate is formed in the first chamber 253. The diluent may be filtered through the filter membrane 274 and may enter the chamber 254 via the diluent stem outlet end 276. The multi-chamber product bags 202 and 203 of FIGS. 3B and 3C also include the diluent filter assembly 261 attached to the bottom end 279 of the product bag 202 and 203. However, any of the product bags disclosed herein may be manufactured, shipped, and/or assembled with or without a diluent filter assembly attached.

Each of FIGS. 3B and 3C illustrates an alternative embodiment of a multi-chamber product bag 202 and 203. The filtration system of the product bag 202 of FIG. 3B is substantially similar to the product bag 100 of FIG. 1, and the filtration system of the product bag 203 of FIG. 3C is substantially similar to the product bag 102 of FIG. 2B. For ease of reference, and to the extent possible, the same or similar components of the product bag 202 of FIG. 3B and the product bag 203 of FIG. 3C will retain the same reference numbers as outlined above with respect to the product bag 100 of FIG. 1 and the product bag 102 of FIG. 2B, respectively, discussed above, although the reference numbers will be increased by 100.

Turning first to FIG. 3B, the product bag 202 includes a bladder 204 defining a first chamber 263 and second chamber 265, where the second chamber 265 is fluidly sealed from the first chamber 263 by a film or a seal 281. The filtration system 206 of the product bag 202 includes a vapor release member and a diluent filter assembly 261. The vapor release member 206 is involved with both sterile-filling the chamber 263 with a solution and permitting vapor removal during lyophilization. As such, the vapor release member 206 may be integrated with, or include, a filter assembly. In this case, the vapor release member 206 may be identical to the filter assembly 106 of the product bag 100 of FIG. 1. The vapor release member 206 of the product bag 202 includes a stem 230 having an inlet end 226 and an outlet end 236, where the outlet end 236 is in fluid communication with the bladder 204. In particular, the outlet end 236 is in fluid communication with the first chamber 263 of the bladder 204. A filter membrane 242 is disposed between the inlet end 226 and the outlet end 236 of the stem 230, and is adapted to sterile-filter a liquid solution while filling the first chamber 253 of the bladder 204. The filter membrane 242 may be a flat filter membrane having an open filter end 244 and a closed filter end 246. The vapor release member 206 is in fluid communication with the first chamber 263 of the bladder 204, and is adapted to release vapor formed in the bladder during lyophilization while maintaining a powder concentrate within the bladder 204, as previously described.

In another embodiment shown in FIG. 3C, a multi-chamber product bag 203 includes a filtration system that may be identical to the filtration system of the product bag 102 of FIG. 2B. The filtration system of the product bag 203 includes a filter assembly 208, which may be identical to the first filter assembly 108, a vapor release member 209, which may be identical to the second filter assembly 109, and a diluent filter assembly 261, which may be identical to the third filter assembly 161. In the embodiment of FIG. 3C, the bladder 215 is defined by first and second chambers 266 and 268, which are sealed from the other chamber by a seal 282 or a film. The diluent filter assembly 261 is fluidly connected to the second chamber 268, and the filter assembly 208 and vapor release member 209 are fluidly connected to the first chamber 266.

Figure 4A:
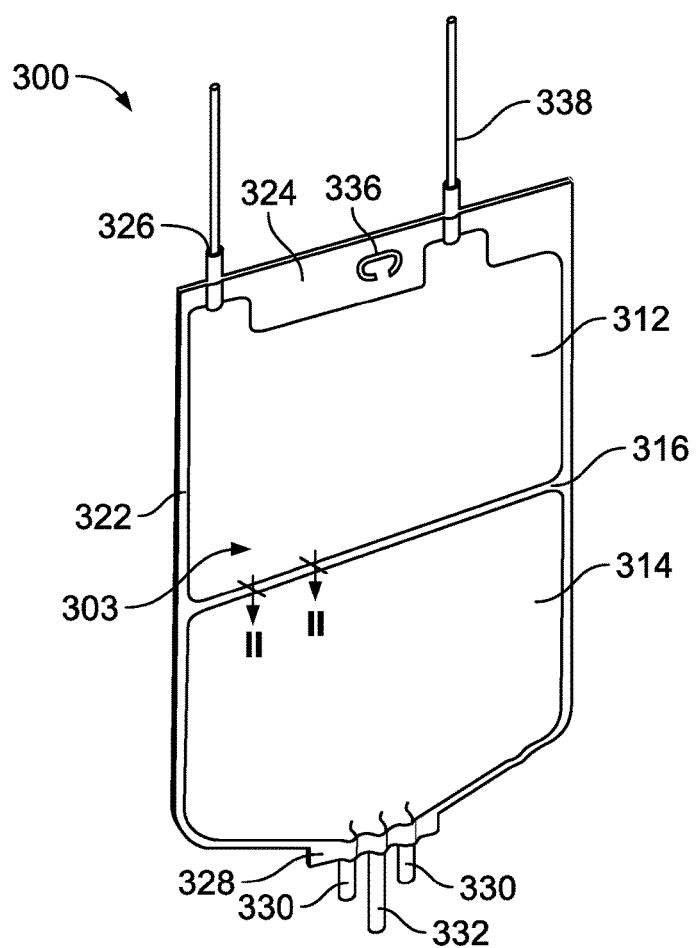
FIG. 4A is a perspective view of a multi-chamber product bag having a peelable seal in accordance with the teachings of the present disclosure.
Figure 4B:
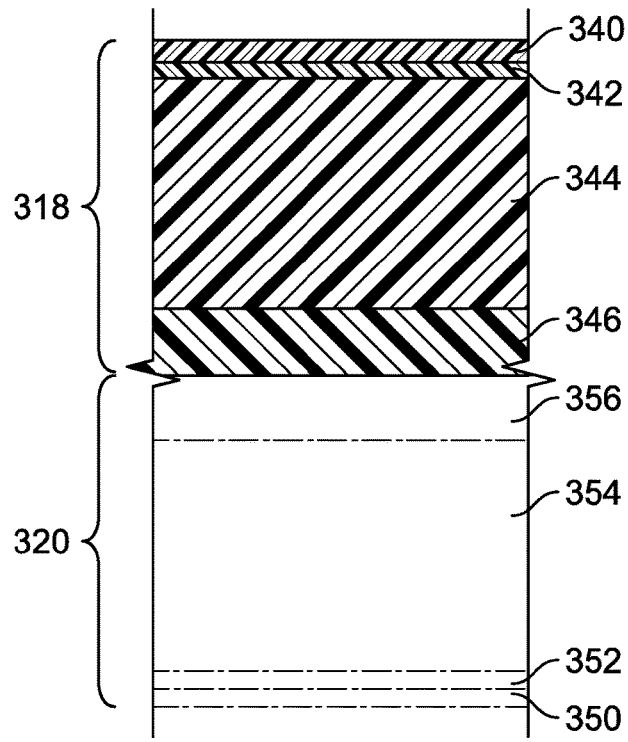
FIG. 4B is a cross-sectional view of an embodiment of a peelable seal film of the product bag of FIG. 4A taken generally along plane II-II.

Referring to FIGS. 4A and 4B, a multi-chamber sterile product bag 300 is generally shown, and may be representative of any one of the product bags 201, 202, or 203 of FIGS. 3A-3C. The product bag 300 includes a chamber 303 separated into two chamber portions 312 and 314 for the separate storage of substances and/or solutions. A peelable seal 316 is provided between the chamber portions 312 and 314. Although in the embodiments illustrated, the product bag 300 includes two chamber portions 312 and 314, it should be appreciated that additional peelable seals may be included to divide the chamber 303 into additional chamber portions. The bag 300 is formed from two sheets of a multi-layer film. A first or front sheet 318 and a second or rear sheet 320 are sealed about the periphery 322 of the bag 300 by, for example, heat sealing. The peelable seal 316, described more fully below, is provided between the sheets 318 and 320 to form the chamber portions 312 and 314.

In the preferred embodiments illustrated in FIGS. 4A and 4B, a top end 324 of the product bag 300 includes a stem 326 equipped with a filter for sterilizing fluid passing through the stem 326 and into the first chamber portion 312. The filtration system can include any of the filters, filters, membranes, and filtration devices described above with respect to FIGS. 1-3C and below with respect to FIGS. 5-20. A bottom end 328 of the product bag 300, may potentially include more one or more tubular ports 330. The tubular port 330 may allow the medical substances contained within the product bag 300 to be discharged to one or more patients. Similarly, the tubular port 330 may allow medicaments to be injected into the bag 300. The tubular port 330 is mounted in the product bag 300 to communicate with the product bag 300 via the chamber portion 314. The port 330 may include a membrane that is pierced by, for example, a cannula or a spike of an administration set for delivery of the contents of the product bag 300 through the administration set to a patient. One of the ports may receive or be replace with, for example, a diluent filter.

In FIG. 4B, the sheets 318 and 320 which form the bag 300 are illustrated in cross-sectional view. Specifically, the seal 316 is illustrated at the junction of the sheet 318 with the sheet 320. The seal 316 is formed such that no communication between the chamber portions 312 and 314 is provided until the seal 316 is broken. That is, the chamber portions 312 and 314 are fluidly isolated from each other when the seal 316 is intact such that fluids and gasses cannot pass from one chamber portion to the other. Rupturing or breaking the peelable seal 316 serves to provide communication between the chamber portions 312 and 314 allowing a mixing of the substances stored therein. The sheets 318 and 320 are flexible and are preferably made of the same materials.

In the illustrated embodiment, the first sheet 318 includes a first layer 340 forming an outer surface or abuse layer of the product bag 300. The first layer 340 may be, for example, a thermoplastic material such as PCCE. A typical thickness of the first layer 340, in a preferred embodiment, is approximately 0.55 mil but may vary, for example, between 0.40 mil and 0.70 mil. A tie layer 342 can be provided to provide a binding layer between the outside layer 340 and a second layer 344 of the sheet 318 which is RF-responsive. Although in a preferred embodiment, the tie layer 342 has a thickness of approximately 0.4 mils, the tie layer 342 may, however, have a varied thickness, for example, between 0.25 mils and 0.55 mils. The tie layer 342 can be a thermoplastic material such as ethyl vinyl acetate (EVA) modified with malic anhydride.

The second layer 344 is an RF-responsive layer that, as discussed below, cooperates with a sealing or inner layer 346 to create the seal 316. The second layer 344 can be any RF-responsive material. In a preferred embodiment, the RF-responsive material is an ethyl vinyl acetate (EVA). It has been found that a layer thickness of approximately 6.2 mils functions satisfactorily. However, the second layer 344 can have a varied thickness of between, for example, at least 5.75 mils and 6.75 mils.

The sealing layer 346 is made of a non-RF responsive material. Preferably, the non-RF responsive layer includes at least two materials having different melting points. In an embodiment, the non-RF-responsive layer is an alloy of styrene-ethylene-butyl-styrene (SEBS) for example, Kraton®, and ethylene polypropylene copolymer. It has been found that if the sealing layer has a thickness of approximately 1.6 mils it functions satisfactorily. However, the thickness may vary, for example, between 1.40 mils and 1.80 mils.

The sealing layer 346 is adjacent the solution side of the container 300 such that when the seal 316 is ruptured, communication is provided between the chamber portions 312 and 314. As noted above, the four-layer film illustrated in FIG. 4D has at least one RF-responsive layer 344 and one non-RF responsive layer 346. A RF field heats a seal bar (not shown) which heats the RF-responsive layer 344 which, in turn, heats the non-RF responsive layer 346 to soften the layer 346, but not liquefy same. A resulting cohesive bond develops from contact between the non-RF responsive layer 346 of the sheet 318 and a corresponding non-RF responsive layer 356 of the sheet 320, but fusion between the layers, which can cause permanent bonding, does not occur.

As previously indicated, the product bag 300 can be formed by folding a single web, such as the sheet 318, or alternatively, the sheet 320 can be further provided in addition to the sheet 318. In the preferred embodiment, the sheet 320 is a four-layer film in which layers 350, 352, 354 and 356 of the sheet 320 substantially correspond to the layers 340, 342, 344 and 346 of the sheet 318, respectively. As a result, the sealing layer 356 of the sheet 320 forms a cohesive bond with the sealing layer 346 of the sheet 318. The cohesive bond formed is the peelable seal 316. It should be appreciated that fewer layers for each of the sheets 318 and 320 than the four-layer film described with reference to FIG. 4B can be used to create the peelable seal 316 of the present invention. Two layers can be used, one layer being RF-responsive and the other layer being non-RF responsive. Reliability and strengthening of the peelable seal 316 may be further enhanced by using corona treatment or an extrusion process.

The peelable seal 316 is preferably formed to withstand external pressure to one or both chamber portions 312 and 314 of the container. Furthermore, the peelable seal 316 is capable of withstanding pressure exerted by dropping the product bag 300 either on its side or if it is dropped flat. Preferably, the peelable seal 316 can withstand rupture from a drop of up to six feet. Post-sterilization of the chamber portions 312 and 314 of the product bag 300 substantially increases the pressure which the peelable seal 316 is capable of withstanding before rupture. More specifically, sterilization can increase seal strength between 40 and 80 percent.

To provide a sterile powder concentrate in a sealed product bag when both chamber portions 312 and 314 are completely empty, the user may first introduce a solution to be lyophilized to the first chamber portion 312 through the filtered stem 326 in the manner described above with reference to the product bags 100, 101, 201, 202 and 203 in FIGS. 1-3C. Subsequently, the filtered stem 326 can be sealed, cut, and integrity tested. If the filter passes the integrity test, the user can determine that the solution in the first chamber portion 312 is sufficiently sterile to continue. Next, the user may lyophilize the solution to form a powdered concentrate sealed in the first chamber portion 312. After lyophilization, the user may next seal and cut a vapor release member 338, which may be a second filtered stem, and test the integrity of the filter of the vapor release member 338. If the filter passes the integrity test, the user can determine that the powder concentrate in the first chamber portion 312 is sufficiently sterile to continue. Next, the user can introduce a diluent to the second chamber portion 314 through an additional diluent stem 332. Subsequently, the diluent stem 332 can be sealed, cut, and the diluent filter integrity tested. If the diluent filter passes the integrity test, the user can determine that the solution in the second chamber portion 314 is sufficiently sterile to continue.

With the first chamber portion 312 containing concentrate and the second chamber portion 314 containing diluent, a user can apply a compressive force to the outside of the product bag 300 in the region of the first chamber portion 312, which creates a hydraulic force applied to the peel seal 316, ultimately breaking the peel seal 316 and causing fluid communication between the first and second chamber portions 312 and 314. Continued manual manipulation of the product bag 300 mixes the concentrate and diluent thoroughly to arrive at a solution ready for patient administration.

While FIGS. 3A-4B illustrate multi-chamber product bags 201, 202, 203, and 300 with two isolated chamber portions in accordance with the present disclosure, other alternatives can include additional chambers an/or additional features. For example, one example of a multi-chamber product bag that can benefit from the present advancements includes that which is disclosed in U.S. Pat. No. 6,165,161, entitled SACRIFICIAL PORT FOR FILLING FLEXIBLE, MULTIPLE-COMPARTMENT DRUG CONTAINER, the entire contents of which are incorporated herein by reference.

Filter Assembly Examples

Any of the following filter assembly examples illustrated in FIGS. 5-20 may be used as one of the filter assemblies of the previously illustrated and described product bags. The filter assembly depicted in FIG. 5 may be representative of any of the filter assemblies 107B, 108, 161, 207, 208, 261, 326, and/or 338 in FIGS. 2A-4B. For illustrative purposes only, the reference numbers of the filter assembly 107A in FIG. 5 correlate with filter assembly 107A in FIG. 2A.

The filter assembly 107A includes a hollow connector 166 that can be used to secure the stem 156A and the filter 155A together. The open inlet end 151 of the filter 155A is sealingly connected to an open outlet end 168 of the hollow connector 166. The connection may be achieved by gluing the open inlet end 151 of the filter 155A to the open outlet end 168 of the connector 166 with, for example, an epoxy resin, a polyurethane resin, a cyanoacrylate resin, a UV curing acrylic adhesive, or a solvent for the material of the hollow connector 166 such as cyclohexanone. In the version depicted, the open outlet end 168 of the connector 166 comprises a hollow cylindrical member that fits inside of and is fixed to the open inlet end 151 of the filter 155A. As such, an outer diameter of the open outlet end 168 of the connector 166 is substantially similar to or slightly smaller than an inner diameter of the open inlet end 151 of the filter 155A. In some versions, the open inlet end 151 of the filter 155A may be welded to the open outlet end 168 of the connector 166 by, for example, heat welding (e.g., introducing a hot conical metal tip into the open inlet end 151 of the filter 155A to partially melt it), laser welding if the hollow connector 166 is made from a material that absorbs laser radiation, mirror welding, ultrasound welding, and friction welding. Alternately, the filter 155A may be inserted into a mold, and a thermoplastic polymer may be injection-molded around it to form the hollow connector 166. Other designs and configurations for connecting the filter 155A to the connector 166 are intended to be within the scope of the present disclosure.

The hollow connector 166 further includes a fluid inlet 169. A pharmaceutical fluid can be fed via a connected fluid supply line, for example, into the fluid inlet 169 of the hollow connector 166. In some versions, the fluid inlet 169 can include a Luer type fitting or other standard medical fitting. The pharmaceutical fluid can then travel through the hollow connector 166 and exit into the filter 155A through the open outlet end 168 of the hollow connector 166. The hollow connector 166 also includes a sealing surface 172 to which the stem 156A is attached. The sealing surface 172 in this version is cylindrical and has a diameter larger than a diameter of the open outlet end 168, and is disposed generally concentric with the open outlet end 168. In fact, in this version, the outer diameter of the sealing surface 172 is generally identical to or slightly smaller than an inner diameter of the stem 156A. So configured, the stem 156A receives the sealing surface 172 and extends therefrom to surround and protect the filter 155A without contacting the surface 164 of the filter 155A. The stem 156A can be fixed to the sealing surface 172 with adhesive (e.g., a UV curing acrylic adhesive), epoxy, welding, bonding, etc. The stem 156A receives the pharmaceutical solution after it passes through the pores 162 in the filter 155A. From there, the now filtered solution passes into the bladder 152.

FIGS. 6-10 illustrate an alternative hollow connector 766, similar to connector 166, for securing the stem 156A and the hollow fiber filter 155A of FIGS. 2A and 5 together. The connector 766 includes an open outlet end 768 carried by a stem structure that extends in a first direction from a bearing plate 777 and is adapted to be sealingly connected to the open inlet end 151 of the filter 155A. The connection may be achieved by gluing the open inlet end 151 of the filter 155A to the open outlet end 768 of the connector 766 with, for example, an epoxy resin, a polyurethane resin, a cyanoacrylate resin, a UV curing acrylic adhesive, or a solvent for the material of the hollow connector 766 such as cyclohexanone. In the version depicted, the stem structure of the open outlet end 768 of the connector 766 comprises a hollow cylindrical member that fits inside of and is fixed to the open inlet end 151 of the filter 155A. As such, an outer diameter of the open outlet end 768 of the connector 766 is substantially similar to or slightly smaller than an inner diameter of the open inlet end 151 of the filter 155A. In some versions, the open inlet end 151 of the filter 155A may be welded to the open outlet end 768 of the connector 766 by, for example, heat welding (e.g., introducing a hot conical metal tip into the open inlet end 151 of the filter 155A to partially melt it), laser welding if the hollow connector 766 is made from a material that absorbs laser radiation, mirror welding, ultrasound welding, and friction welding. Alternately, the filter 155A may be inserted into a mold, and a thermoplastic polymer may be injection-molded around it to form the hollow connector 766. Other designs and configurations for connecting the filter 155A to the connector 766 are intended to be within the scope of the present disclosure.

The hollow connector 766 further includes a fluid inlet 769, which is also a stem structure, extending in a second direction (opposite the first direction) from the bearing plate 777. A pharmaceutical fluid can be fed via a connected fluid supply line, for example, into the fluid inlet 769 of the hollow connector 766. In some versions, the fluid inlet 769 can include a Luer type fitting or other standard medical fitting. The pharmaceutical fluid can then travel through the hollow connector 766 and exit into the filter 155A through the open outlet end 768 of the hollow connector 766.

The hollow connector 766 also includes a sealing surface 772 to which the stem 156A is attached. The sealing surface 772 in this version is a cylindrical shroud extending from the bearing plate 777 in the first direction and has a diameter larger than a diameter of the open outlet end 768. The sealing surface 772 is disposed generally concentric with the open outlet end 768. As such, in this embodiment, the shroud of the sealing surface 772 surrounds the stem structure of the open outlet end 768 such that an annular gap 779 resides between the two. In fact, in this version, the outer diameter of the sealing surface 772 is generally identical to or slightly smaller than an inner diameter of the stem 156A. So configured, the sealing surface 772 of the connector 766 can be received by the stem 156A such that the stem 156A extends therefrom to surround and protect the filter 155A without contacting the surface 164 of the filter 155A. The stem 156A can be fixed to the sealing surface 772 with adhesive (e.g., a UV curing acrylic adhesive), epoxy, welding, bonding, etc. The stem 156A receives the pharmaceutical fluid after it passes through the pores 162 in the filter 155A. From there, the now filtered fluid passes into the bladder 152 in the same manner described above with respect to FIGS. 1-5.

While the foregoing version of the filter 155A has been described as including a single filter membrane 155A, in other embodiments within the scope of the present disclosure, the filter 155A may include multiple filter membranes 155A. A few non-limiting examples of multiple membrane filters will be discussed below. Finally, as described with respect to the product bags in FIGS. 1-4A, the connector 166 in FIG. 5 can include a sterile closure cap 154 covering the solution inlet 124 to prevent contaminants from entering the product bag prior to being filled.

In one version of the foregoing assembly of FIG. 5, and as mentioned, the stem 156A includes an inner diameter that is larger than an outer diameter of the filter membrane 155A, and the stem 156A includes a longitudinal dimension that is larger than a longitudinal dimension of the filter membrane 155A. As such, when the stem 156A and filter membrane 155A are assembled onto the connector 166, the filter membrane 155A resides entirely within (i.e., entirely inside of) the stem 156A and a gap exists between the inner sidewall of the stem 156A and the outer sidewall of the filter membrane 155A. As such, fluid passing into the filter membrane 155A passes out of the plurality of pores 162 and flows without obstruction through the gap and along the inside of the stem 156A to the bladder. In some versions, the stem 156A can be a flexible tube, a rigid tube, or can include a tube with portions that are flexible and other portions that are rigid. Specifically, in some versions, a stem 156A with at least a rigid portion adjacent to the filter membrane 155A can serve to further protect the filter membrane 155A and/or prevent the filter membrane 155A from becoming pinched or kinked in a flexible tube. In other versions, such protection may not be needed or desirable. In one embodiment, the stem 156A has an internal diameter in the range of approximately 2.5 mm to approximately 8 mm, and a longitudinal dimension in the range of approximately 5 cm to approximately 30 cm. In one embodiment, the internal diameter of the stem 156A is about 0.2 to about 3 mm larger than the outer diameter of the filter membrane 155A. And, the filter membrane 155A has an outer diameter in the range of approximately 2.3 mm to approximately 5 mm, a longitudinal dimension in the range of approximately 3 cm to approximately 420 cm, and a wall thickness in the range of approximately 150 µm to approximately 500 µm. Furthermore, in one version each of the plurality of pores 162 in the filter membrane 155A have a diameter less than or equal to approximately 0.2 microns. In some versions, each pore has a diameter less than or equal to a value in a range of approximately 0.1 microns to approximately 0.5 microns, for instance, approximately 0.2 to approximately 0.4 microns. In some versions, each pore has a diameter that is less than or equal to approximately 0.22 microns. In some versions, each pore has a diameter that is less than or equal to a value in a range of approximately 0.1 microns to approximately 0.2 microns. In some versions, each pore has a diameter that is less than or equal to a value in a range of approximately 0.1 microns to approximately 0.22 microns. These pore sizes coupled with the disclosed geometrical dimension of the stem 156A and filter membrane 155A ensure acceptable flow rates through the filter membrane 155A for filling the product bags with patient injectable solutions such as sterile water, sterile saline, etc. In other versions, any or all of the dimensions could vary depending on the specific application.

Suitable materials for the filter membrane 155A can include nylon, polyolefins (e.g., PE, PP, PET), polyvinylidene fluoride, polymethylmethacrylate, polyacrylonitrile, polysulfone, and polyethersulfone. In some embodiments within the scope of the present disclosure, the filter 155A may be comprised of a blend of polysulfone or polyethersulfone and polyvinylpyrrolidone. In other embodiments within the scope of the present disclosure, the filter membrane 155A can include a polymer containing cationic charges, e.g. polymers bearing functional groups like quaternary ammonium groups. A suitable example for such polymers is polyethyleneimine. The filter membrane 155A may be manufactured by known techniques including, e.g., extrusion, phase inversion, spinning, chemical vapor deposition, 3D printing, etc. Suitable materials for the stem 156A include PVC, polyesters like PET, poly(meth)acrylates like PMMA, polycarbonates (PC), polyolefins like PE, PP, or cycloolefin copolymers (COC), polystyrene (PS), silicone polymers, etc.

Additional details regarding some possible versions of the filter and the specific construction of the membrane, for example, can be found in European Patent Application No. EP16152332.9, entitled FILTER MEMBRANE AND DEVICE, filed Jan. 22, 2016, and additionally in PCT/EP2017/051044, entitled FILTER MEMBRANE AND DEVICE, filed Jan. 19, 2017, the entire contents of each of which are expressly incorporated herein by reference.

Thus far, the hollow fiber membrane 155A in FIG. 5, for example, has been described as being located within the stem 156A. In other embodiments, the filter 155A may include its own housing or other support structure, which is coupled to the stem 156A either in place of the connector 166 in FIG. 5 or connector 766 in FIGS. 6-10, or at a location between two portions of the stem 156A.

Figure 11:
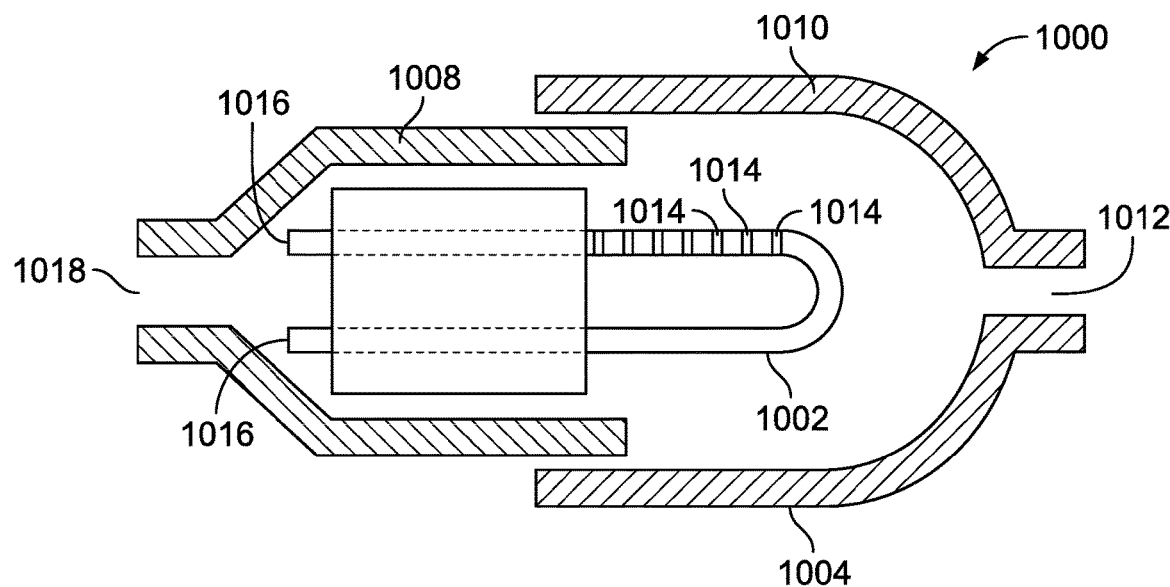
FIG. 11 is a front view of a filter having a single looped hollow fiber membrane contained within a filter body used with any of the product bags of FIGS. 1-4A.

For example, FIG. 11 is a front view of a filter assembly 1000 for a product bag (not pictured) having a single U-shaped hollow fiber filter membrane 1002 contained within a filter body 1004. The filter membrane 1002 is secured to a filter membrane housing 1006 in the U-shaped configuration with an adhesive (i.e., a UV curing acrylic adhesive), an epoxy, welding, bonding, or other means. The filter membrane housing 1006 is connected to the filter body 1004 at an outlet portion 1008 of the filter body 1004. An inlet portion 1010 is sealably connected to the outlet portion 1008 of the filter body 1004 at a joint or other seam. The inlet portion 1010 of the filter body 1004 has an inlet 1012 by which a pharmaceutical fluid may enter the filter assembly 1000. The pharmaceutical fluid then enters the filter membrane 1002 through a plurality of pores 1014, travels through the filter membrane 1002, exits the filter membrane 1002 at filter membrane outlets 1016, and exits the filter body 1004 at filter outlet 1018. The filter outlet 418 may then be connected to the bladder (not pictured) via the stem 256 of a product bag (not pictured). In FIG. 11, the flow of fluid through the assembly 1000 has been described as moving from the inlet 1012 of the inlet portion 1010 to the outlet 1018 of the outlet portion 1008. However, the same assembly 400 could be used in the opposite direction such that fluid enters the outlet 1018 of the outlet portion 1008 and exits the inlet 1012 of the inlet portion 1010. In this alternative configuration, fluid would first enter the inlet 1018, pass into the filter membrane 1002 at the filter membrane outlets 1016, and exit through the pores 1014 and finally the inlet 1012.

Figure 12:
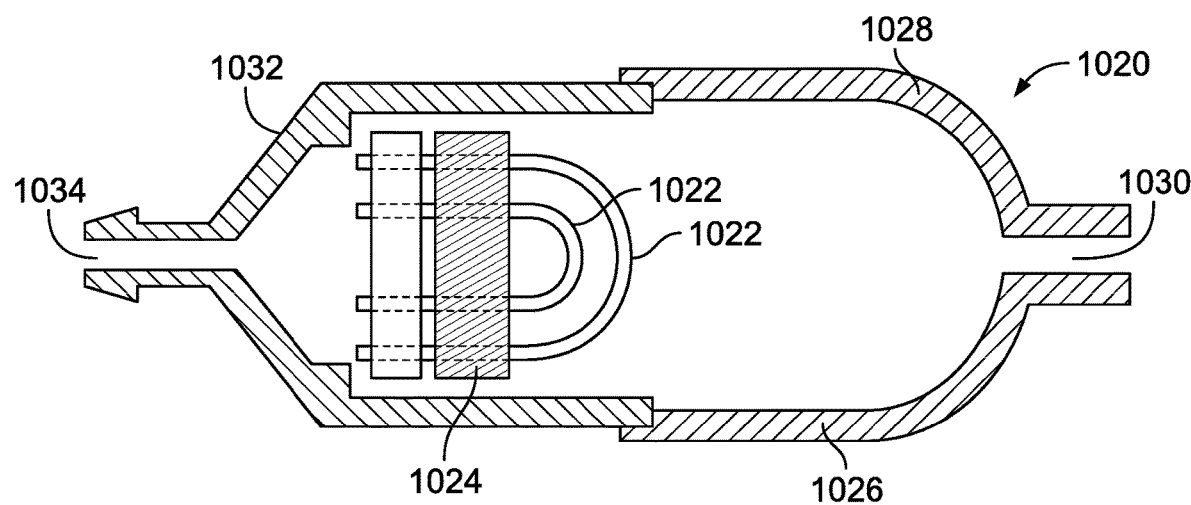
FIG. 12 is a front view of a filter having a plurality of looped hollow fiber membranes contained within a filter body used with any of the product bags of FIGS. 1-4A.

FIG. 12 is an alternate embodiment of the filter assembly 1000 depicted in FIG. 11. In FIG. 12, the filter 1020 includes two U-shaped hollow fiber filter membranes 1022 are secured to a filter membrane housing 1024 in the U-shaped configuration with an adhesive (i.e., a UV curing acrylic adhesive), an epoxy, welding, bonding, or some other means. The filter membranes 1022 and filter membrane housing 1024 are contained within a filter body 1026 having an inlet portion 1028 with inlet 1030 sealably connected to an outlet portion 1032 having filter outlet 1034. In other embodiments, a filter may include more than two U-shaped hollow fiber filter membranes arranged as depicted in FIGS. 11 and 12. In FIG. 12, like in FIG. 11, the flow of fluid through the assembly 1000 has been described as moving from the inlet portion 1028 to the outlet portion 1032. However, the same assembly 1000 could be used in the opposite direction such that fluid enters the outlet portion 1032 and exits the inlet portion 1028 as described above relative to FIG. 11.

FIG. 13 is a further alternative filter assembly. Specifically, in FIG. 13, a plurality of linear membrane filters 502 are secured directly together in a parallel side-by-side configuration for what can be referred to as a fiber bundle. The filters 502 in FIG. 13 can be secured together with adhesive (i.e., a UV curing acrylic adhesive), epoxy, welding, bonding, etc. In other versions, the plurality of filters 502 can be manufactured together as one piece by way of any of the manufacturing techniques described above.

FIG. 14 provides another alternative in which a securement device 504 includes a number of blocks defining a plurality of grooves 506 identical to the number of hollow fiber membrane filters 502. The blocks of the securement device 504 may be sandwiched together and used to hold the plurality of hollow fiber membrane filters 502 in the side-by-side configuration. The securement device 504 depicted in FIG. 14 allows for two sets of the hollow fiber membrane filters 502 of FIG. 13 to be stacked relative to each other. The fiber bundle including the membrane filters 502 and the securement device 504 may be placed in a filter body, such as that discussed with respect to FIGS. 11 and 12.

Figure 15:
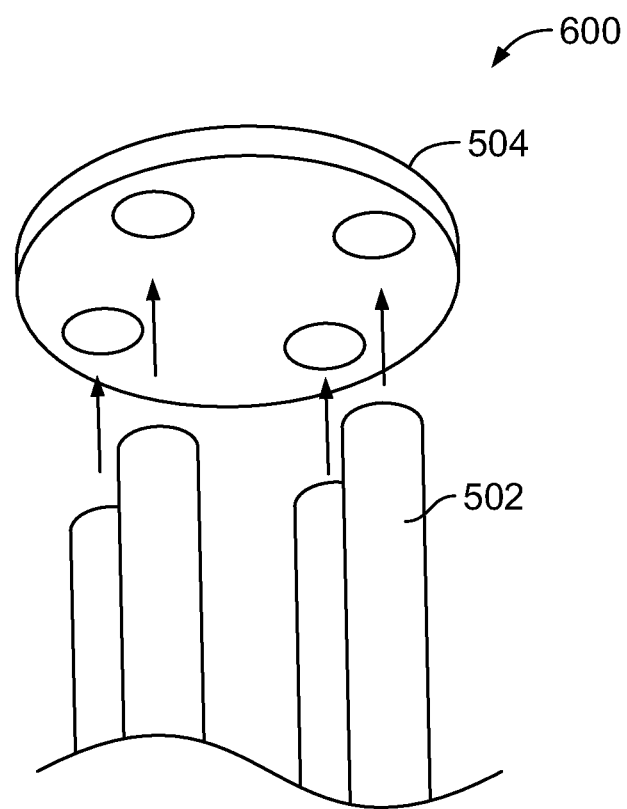
FIG. 15 is an isometric view of a fiber bundle secured in a circular holder used with any of the product bags of FIGS. 1-4A having a plurality of hollow fiber membranes.

FIG. 15 is an isometric view of another version of a fiber bundle 600 for a product bag (not pictured) having a plurality of parallel hollow fiber membrane filters 502 similar to FIGS. 13 and 14, but wherein the parallel filters 502 are arranged in a circular pattern by a circular holder 504. The fiber bundle 600 may be placed in a filter body, such as that discussed with respect to FIGS. 11 and 12.

Figure 16:
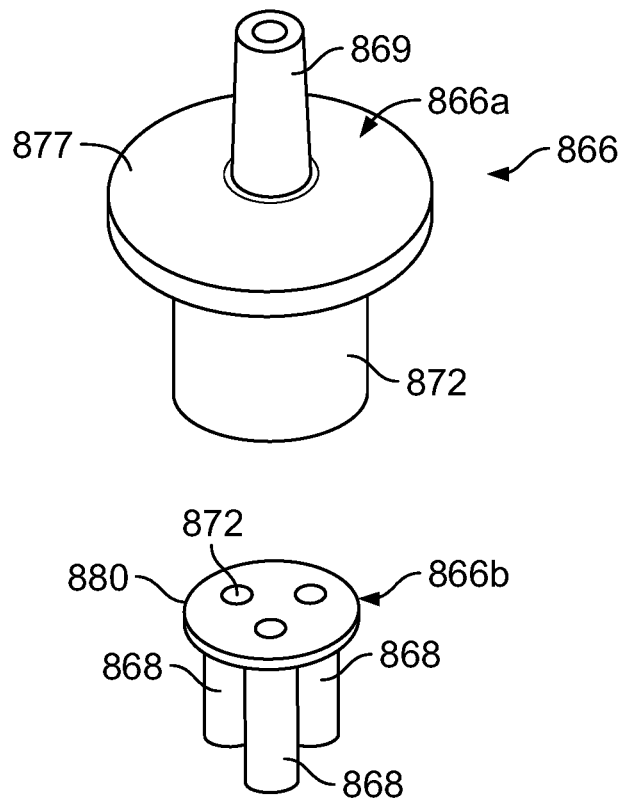
FIG. 16 is an exploded perspective view of an alternative connector for use with a three-filter filter bundle.
Figure 17:
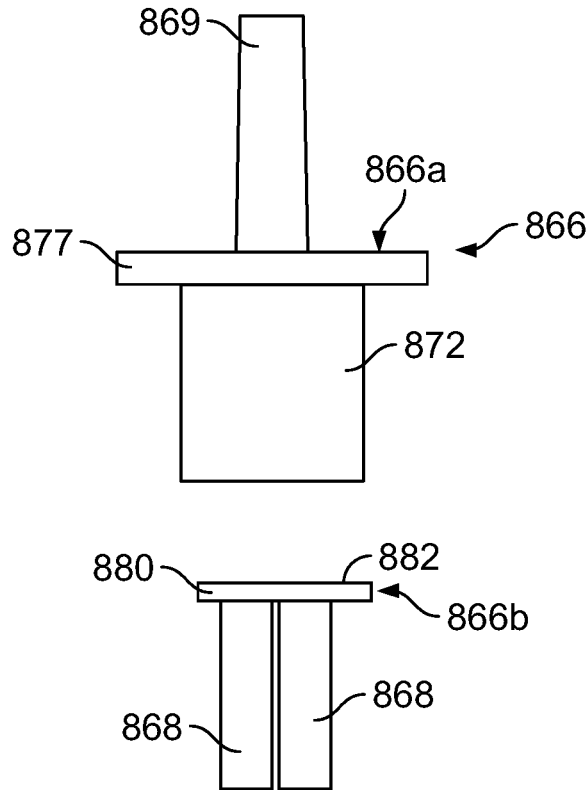
FIG. 17 is a side exploded view of the connector of FIG. 16.

FIGS. 16 and 17 and FIGS. 18-20 illustrate two additional devices for coupling fiber bundles to a stem in accordance with the present disclosure. FIGS. 16 and 17 disclose a connector 866 for connecting a three-fiber bundle to a stem. Specifically, the connector 866 includes a first hollow body 866a and a second hollow body 866b. The first body 866a includes a solution inlet 869, which is a stem structure, extending from a bearing plate 877. A pharmaceutical fluid can be fed via a connected fluid supply line, for example, into the fluid inlet 869 of the first hollow body 866a of the connector 866. In some versions, the fluid inlet 869 can include a Luer type fitting or other standard medical fitting.

The hollow connector 866 also includes a sealing surface 872 to which the stem 156A is attached. The sealing surface 872 in this version is a cylindrical shroud extending from the bearing plate 877 in a direction opposite to a direction of extension of the fluid inlet 869. The sealing surface 872 is disposed generally concentric with the fluid inlet 869. As such, in this embodiment, the shroud of the sealing surface 872 defines a cylindrical cavity (not shown in the drawings) for receiving a portion of the second hollow body 866b of the connector 866.

The second hollow body 866b, as depicted, includes a support plate 880 and three open outlet ends 868 extending from the support plate 880. Additionally, the support plate 880 includes an outer diameter that is essentially the same as or slightly smaller than an inner diameter of the cavity of the shroud of the sealing surface 872 such that when assembled, the support plate 880 is positioned into the cavity. In one version, the support plate 880 includes a seal member 882 around its periphery to form a fluid tight seal with the inner surface of the shroud of the sealing surface 872 when inserted into the cavity. Friction, adhesive, or some other means may retain the support plate 880 in connection with the shroud of the sealing surface 872.

As mentioned, the second body 866*b* includes three open outlet ends 868 extending from the support plate 880. Each open outlet end 868 is adapted to be sealingly connected to an open inlet end 151 of one of three filters 155A. The connection may be achieved by gluing open inlet ends 151 of the filters 155A to the open outlet ends 868 with, for example, an epoxy resin, a polyurethane resin, a cyanoacrylate resin, a UV curing acrylic adhesive, or a solvent for the material of the hollow connector 766 such as cyclohexanone. In the version depicted, the stem structure of the open outlet ends 868 of the connector 866 comprises a hollow cylindrical member that fits inside of and is fixed to the open inlet ends 151 of the filters 155A. As such, an outer diameter of the open outlet ends 868 is substantially similar to or slightly smaller than an inner diameter of the open inlet ends 151 of the filters 155A. In some versions, the filters 155A may be welded to the open outlet ends 868 of the connector 866 by, for example, heat welding (e.g., introducing a hot conical metal tip into the open inlet ends 151 of the filters 155A to partially melt it), laser welding if the hollow connector 866 is made from a material that absorbs laser radiation, mirror welding, ultrasound welding, and friction welding. Alternately, the filters 155A may be inserted into a mold, and a thermoplastic polymer may be injection-molded around it to form the hollow connector 866. Other designs and configurations for connecting the filters 155A to the open outlet ends 868 are intended to be within the scope of the present disclosure.

Finally, as with previously described embodiments, the sealing surface 872 of the connector 866 can be received by the stem 156A such that the stem 156A extends therefrom to surround and protect the filters 155A without contacting the surfaces 164 of the filters 155A. The stem 156A can be fixed to the sealing surface 872 with adhesive (e.g., a UV curing acrylic adhesive), epoxy, welding, bonding, etc. The stem 156A receives the pharmaceutical solution after it passes through the pores 162 in the filter 155A. From there, the now filtered solution passes into the bladder 152 in the same manner described above with respect to FIGS. 1-5.

Figure 18:
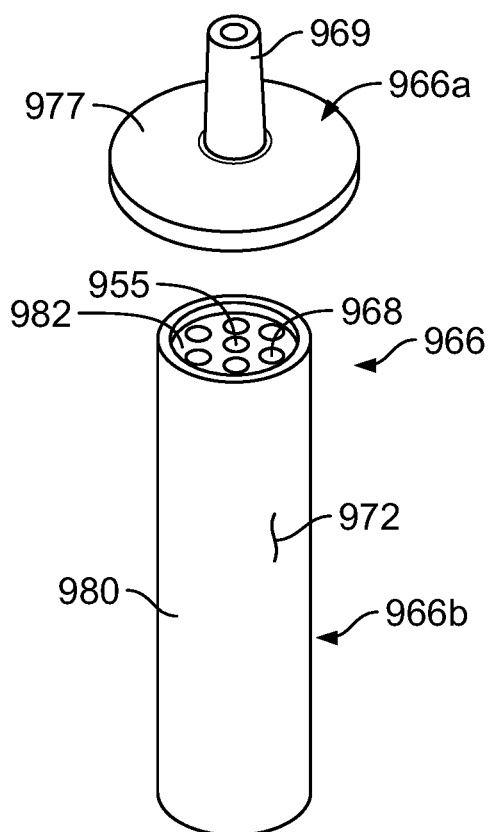
FIG. 18 is a exploded perspective view of another alternative connector for use with a seven-filter filter bundle.
Figure 19:
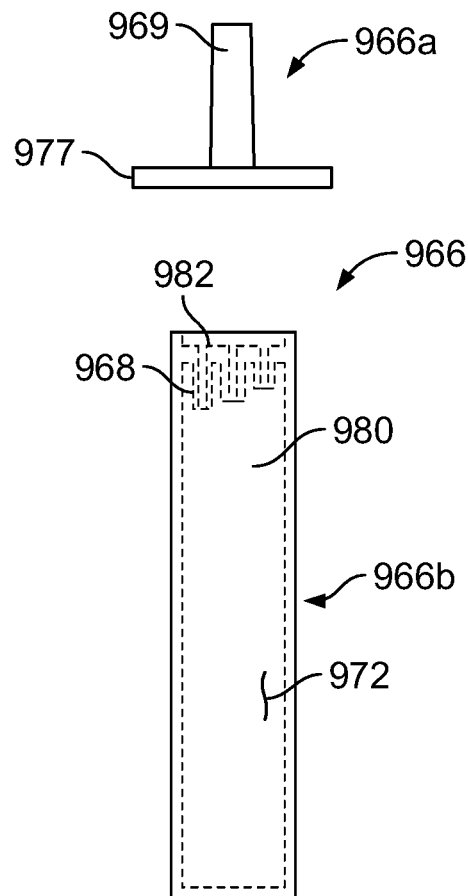
FIG. 19 is a side exploded view of the connector of FIG. 18.
Figure 20:
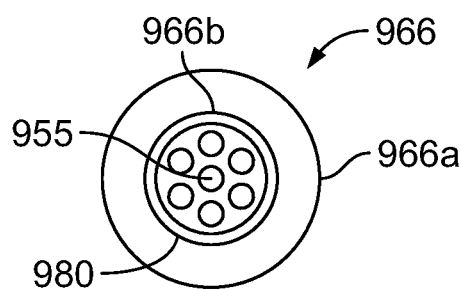
FIG. 20 is a bottom view of the connector of FIG. 19.

FIGS. 18-20 discloses a connector 966 for connecting a seven-fiber bundle to a stem. Specifically, the connector 966 includes a first hollow body 966*a* and a second hollow body 966*b* that can be connected to the first hollow body 966*a* with an adhesive or via other means. The first body 966*a* includes a solution inlet 969, which is a stem structure, extending from a bearing plate 977. A pharmaceutical fluid can be fed via a connected fluid supply line, for example, into the fluid inlet 969 of the first hollow body 966*a* of the connector 966. In some versions, the fluid inlet 969 can include a Luer type fitting or other standard medical fitting.

The second hollow body 966*b*, as depicted, includes a hollow cylindrical support collar 980 in which seven hollow fiber membrane filters 955 can be disposed parallel to each other, as shown in FIGS. 18 and 20. In one version, the support collar 980 can include a support plate 982 carrying seven open outlet ends 968 extending into the collar 980 for connecting to the filters 955 in a manner similar to that described above regarding FIGS. 16 and 17. The connection may be achieved by gluing the filters 955 to the open outlet ends 968 with, for example, an epoxy resin, a polyurethane resin, a cyanoacrylate resin, a UV curing acrylic adhesive, or a solvent for the material of the hollow connector 966 such as cyclohexanone. In the version depicted, the stem structure of the open outlet ends 868 of the connector 866 comprises a hollow cylindrical member that fits inside of and is fixed to the filters 955. As such, a diameter of the open outlet ends 968 is substantially similar to or slightly smaller than an inner diameter of the filters 955. In some versions, the filters 955 may be welded to the open outlet ends 968 of the connector 966 by, for example, heat welding (e.g., introducing a hot conical metal tip into the filters 955 to partially melt it), laser welding if the hollow connector 966 is made from a material that absorbs laser radiation, mirror welding, ultrasound welding, and friction welding. Alternately, the filters 955 may be inserted into a mold, and a thermoplastic polymer may be injection-molded around it to form the hollow connector 966. Other designs and configurations for connecting the filters 955 to the open outlet ends 968 are intended to be within the scope of the present disclosure.

Finally, the collar 980 of this embodiment includes a sealing surface 972 that can be received by the stem 156A such that the stem 156A extends therefrom. The stem 156A can be fixed to the sealing surface 972 with adhesive (e.g., a UV curing acrylic adhesive), epoxy, welding, bonding, etc. The stem 156A receives the pharmaceutical fluid after it passes through the pores 162 in the filters 955. From there, the now filtered fluid passes into the bladder 152 in the same manner described above with respect to FIGS. 1-3C.

Lyophilization Process

Figure 21:
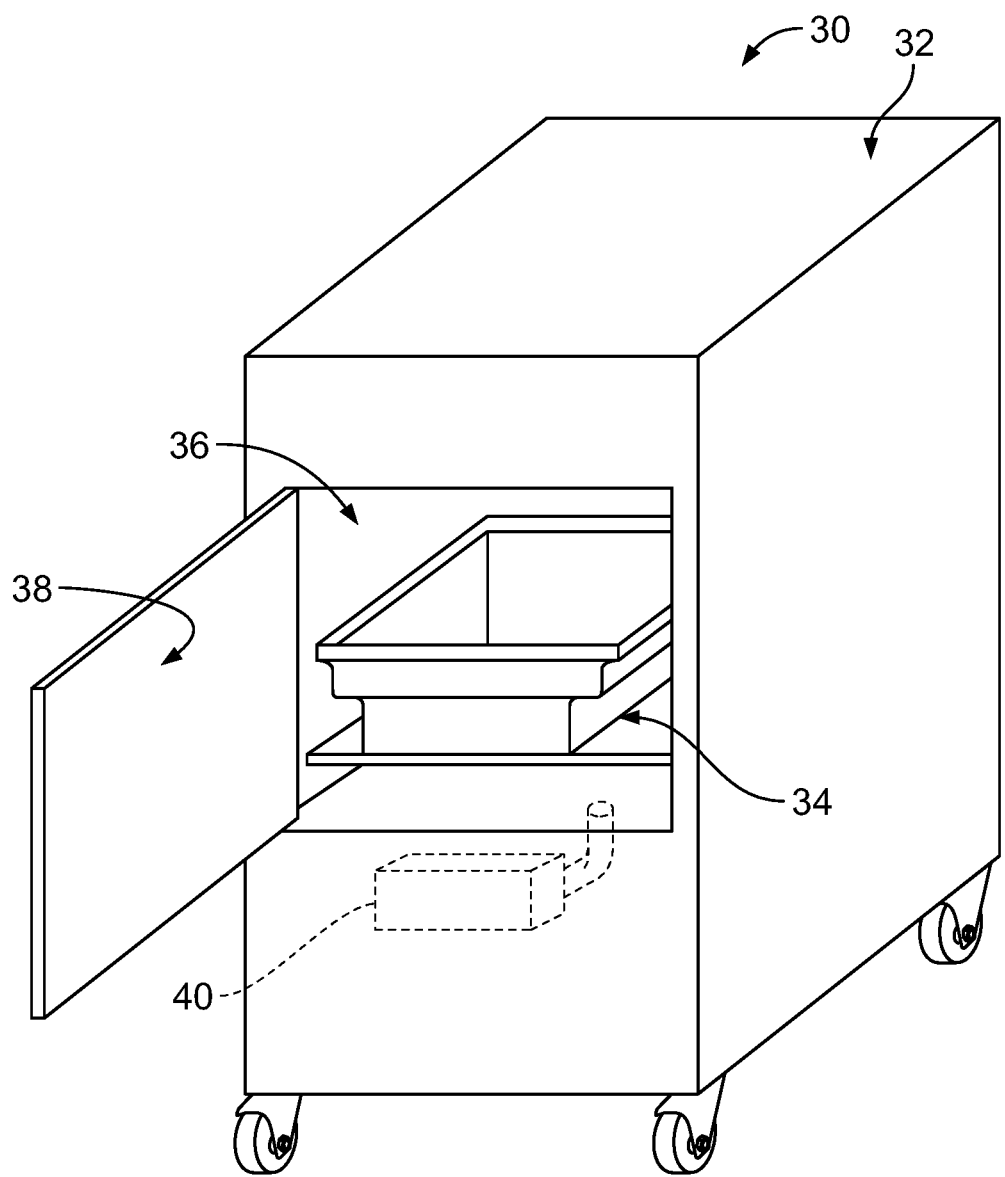
FIG. 21 is a perspective view of an example lyophilization system with a freeze-drying machine.

FIG. 21 depicts a system 30 used for lyophilizing a liquid, which includes a freeze-drying machine 32 accommodating a bin 34 that is adapted to hold one or more product bags containing the liquid. The freeze-dryer 32 defines a lyophilization chamber 36 that may be selectively opened and closed with a door 38, for example, in a conventional manner. The bin 34 is disposed within the lyophilization chamber 36 such that any material carried within the product bag can be lyophilized after the door 38 is closed and the freeze-drying machine 32 is activated. To lyophilize the material in the product bag, the freeze-drying machine 32 reduces the temperature within the lyophilization chamber 36 to a temperature in the range of approximately negative fifty degrees Celsius (−50° C.) to approximately negative eighty degrees Celsius (−80° C.), for example. Then, the ambient pressure of the lyophilization chamber 36 is reduced with a vacuum pump 40, for example, to a pressure that is substantially less than atmospheric pressure, such as a pressure in the range of approximately 1.33 Pa (0.01 Torr) to approximately 133 Pa (1 Torr). Other ranges between atmospheric pressure and absolute vacuum are intended to be within the scope of the present disclosure. With the ambient pressure reduced, a sufficient amount of heat is added to the lyophilization chamber 36 to sublimate the frozen water in the liquid from a solid to a gas. The gas may be removed from the material and dissipates out of the product bag through the vapor release member and/or filter assembly. The pressure within the lyophilization chamber 36 can then be increased or returned to the ambient pressure that is outside of the lyophilization chamber 36, and the product bag containing the dried material can be removed from the freeze-drying machine 32.

After a suitable lyophilization cycle, the freeze-drying machine 32 then raises the ambient pressure within the lyophilization chamber 36. In some embodiments, the pressure in the lyophilization chamber 36 can be raised by deactivating the vacuum pump 40 and opening a vent, for example, to allow the pressure to stabilize relative to the pressure outside the freeze-drying machine 32. In some embodiments, the pressure in the lyophilization chamber 36 is raised to be substantially equal to atmospheric pressure, i.e., 101 kPa. The product bag can then be safely removed from the lyophilization chamber 36 and transported about the laboratory or production facility without concern of risk of contaminating the lyophilized material sealed within the product bag.

Figure 22:
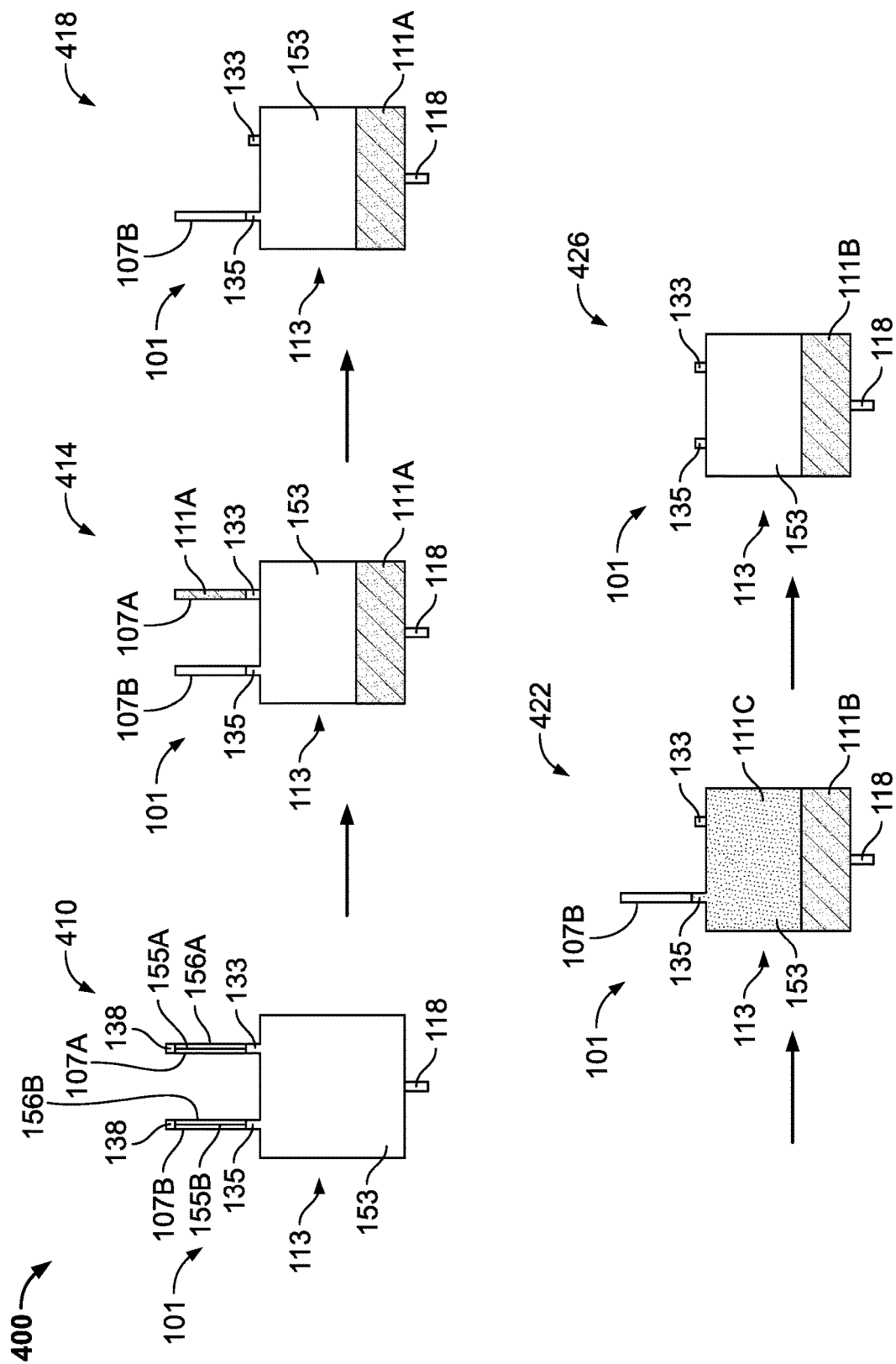
FIG. 22 is a first exemplary schematic for providing a sterile powder in a sealed, single-chamber product bag by lyophilization in accordance with the teachings of the present disclosure.

The schematic illustration of FIG. 22 shows a method 400 of providing a sterile powder in a closed container by lyophilization. As described above with respect to any of FIGS. 1-20, each of the filters, filter membranes, filtration devices, etc., are equipped to sterilize a solution and/or a diluent as the solution and/or diluent passes there through and into the respective chamber. This introduction of the solution can be achieved either manually, automatically, or semi-automatically. One possible automatic system and process that may be utilized is disclosed in PCT/US17/14264, entitled METHOD AND MACHINE FOR PRODUCING STERILE SOLUTION PRODUCT BAGS, the entire contents of which are incorporated herein. For illustrative purposes, the product bag 101 of FIG. 2A is depicted in the process 400 of FIG. 22.

At an initial phase or step 410 of the process 400, an empty product bag 101 having a sterile interior environment 153 is initially delivered to a user entirely empty. That is, the chamber 153 of the bladder 113 is devoid of any material and, moreover, has been pre-sterilized through conventional sterilization techniques including, for example, steam sterilization, gamma, terminal-sterilization, or any other sterilization process. At a filling phase 414, the method includes filling the chamber 153 of the product bag 101 with a liquid solution 111A through a first filter assembly 107A. As previously described, the product bag 101 includes a bladder 113 defining the chamber 153, a first stem 156A containing the first filter 155A, and a second stem 156B containing a second filter 155B. A first port 133, or "cut and seal area," fluidly connects the first stem 156A to the chamber 153 of the bladder 113, and a second port 135 fluidly connects the second stem 156B to the chamber 153 of the bladder 113. In one version where the stems 156A and 156B include a sealing knob 138, as depicted in FIG. 1, the filling phase 414 simply requires removing the knob 138 before introducing a filling port to the stem 104. In other embodiments that include a septum or membrane, the filling port is simply introduced into the stem 156A to pierce the septum or membrane and begin introducing solution to the chamber 153. At the end of the filling phase 414, the product bag 101 is a liquid-filled product bag when the chamber 153 of the bladder 113 contains the liquid solution 111A.

Once the desired amount of solution 111A is added to the chamber 153, the process 400 enters a first integrity testing phase 418, which includes sealing the liquid-filled product bag 101 at the first port 133, and then removing the first stem 156A containing the first filter 155A from the liquid-filled product bag 101. The stem 156A is sealed and cut at the "seal-and-cut" portion 133, which may be considered the port 133 of the stem 156A, as discussed above. This ensures that the stem 156A and the bladder 113 are completely sealed before removing the stem 156A. After removing the first stem 156A, the method may include performing an integrity test on the first filter 155A to ensure that the first filter 155A adequately filtered the liquid solution 111A during the filling phase 414, and that the liquid-filled product bag 101 contains a sterile solution 111A. This may involve correlating an integrity of the liquid solution 111A of the liquid-filled product bag 101 to an integrity of the first filter 155A based on an outcome of the integrity test. If the filter 155A passes the test, the sterility of the solution 111A introduced into the chamber 153 is confirmed. If the filter 155A does not pass the test, the solution 111A and product bag 101 may have to be discarded as the sterility of the solution 111A may be considered compromised or of lesser than desired sterility. Steps taken during phases 410, 414, and 418 are repeated to start over with a new pre-sterilized product bag. In those instances where the filter 155A passes the filter integrity test, the product bag 101 and solution 111A can be lyophilized.

At a lyophilization phase 422, the method includes removing the liquid from the liquid solution 111A of the liquid-filled product bag 101 by lyophilizing the liquid-filled product bag 101. Lyophilizing the liquid-filled product bag 101 includes freeze-drying the liquid-filled product bag 101 in a pressurized lyophilization chamber, such as the chamber 36 of the freeze-drying machine 32 of FIG. 21. The frozen liquid of the liquid-filled product bag 101 sublimes to a vapor 111C, and the vapor 111C is removed through the second stem 156B to produce a powder-filled product bag 101, i.e., when the chamber 153 of the bladder 113 contains a powder concentrate 111B. Optionally, the method may include inserting the liquid-filled product bag 101 into a rigid container prior to inserting the product bag 101 into the lyophilization chamber. The container for holding the product bag 101 during lyophilization is described further below with reference to FIG. 25.

After removing the liquid from the solution contained in the product bag 101 during the lyophilization phase 422, the process may enter a final phase 426 where the method includes sealing the powder-filled product bag 101 at the second port 135, and removing the second stem 156B containing the second filter 155B from the product bag 101. At the final phase 426, the second stem 156B and second filter 155B are removed without compromising the environment of the bladder 113 by methods previously described. After removing the second stem 156B, the method may include performing an integrity test on the second filter 155B in a similar manner previously described in connection to the first integrity testing phase 418 of the first filter 155A. To ensure the powder concentrate 111B is sterile, the method may include correlating an integrity of the sterile powder 111B of the powder-filled product bag 101 to an integrity of the second filter 155B based on an outcome of the integrity test.

Figure 23:
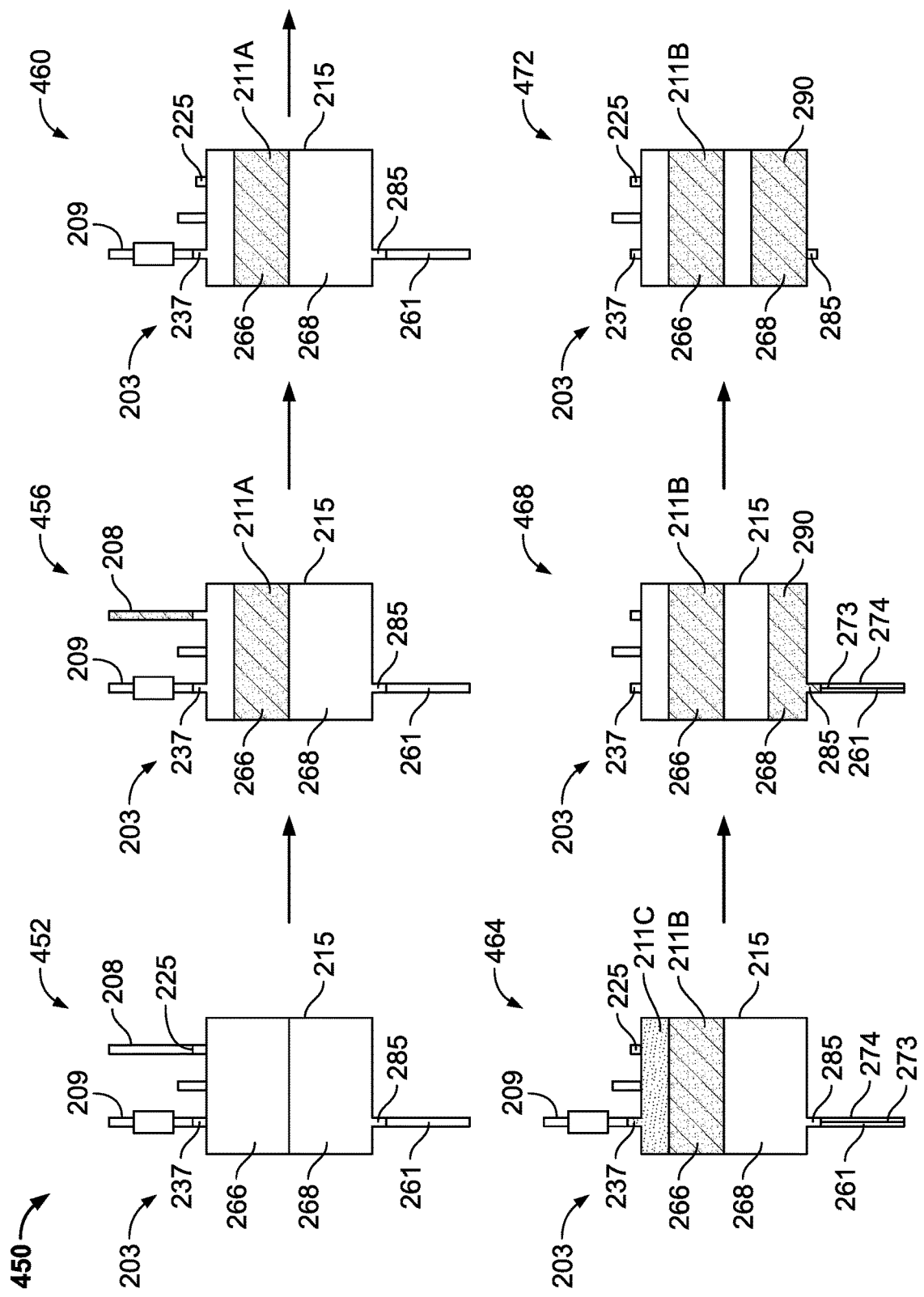
FIG. 23 is a second exemplary schematic for providing a sterile powder in a sealed chamber of a two-chamber product bag by lyophilization in accordance with the teachings of the present disclosure.

Turning now to FIG. 23, a process 450 for filling a multi-chamber product bag, such as the product bag 203 of FIG. 3C, with a sterile powder is illustrated. With the exception of the multi-chamber construction of the product bag 203, phases 452, 456, 460, and 464 of the process 450 may be identical to the respective phases 410, 414, 418, 422, and 426 of the process 400 in FIG. 22 and therefore those steps will not be repeated. Additional phases and/or steps related to the multi-chamber product bag process 450 include a diluent filling phase 468. The diluent filling phase 468 includes filling a second chamber 268 of the bladder 215 with a diluent 290 through a third filter 274 disposed within a third stem 273. A third port 285, which may be the same or separate from an inlet of the second chamber 268, fluidly connects the third stem 273 to the second chamber 268, and the second chamber 268 is fluidly sealed from the chamber 266 containing the powder concentrate 211B.

At a final phase 472, the second chamber 268 is a diluent or liquid-filled second chamber 268 when the second chamber 268 contains the diluent 290. The method may include sealing the liquid-filled second chamber 268 at the third port 285 and removing the third stem 273 from the product bag 203 after filling the second chamber 268. After removing the third stem 273, the method may include performing an integrity test on the third filter 274 to ensure that the third filter 274 adequately filtered the diluent 290 during the diluent filling phase 468, and that the diluent-filled chamber 268 contains a sterile diluent 290. To do so, the method includes correlating an integrity of the diluent 290 of the diluent-filled chamber 268 to an integrity of the third filter 273 based on an outcome of the integrity test, such as the integrity test previously described.

Figure 24:
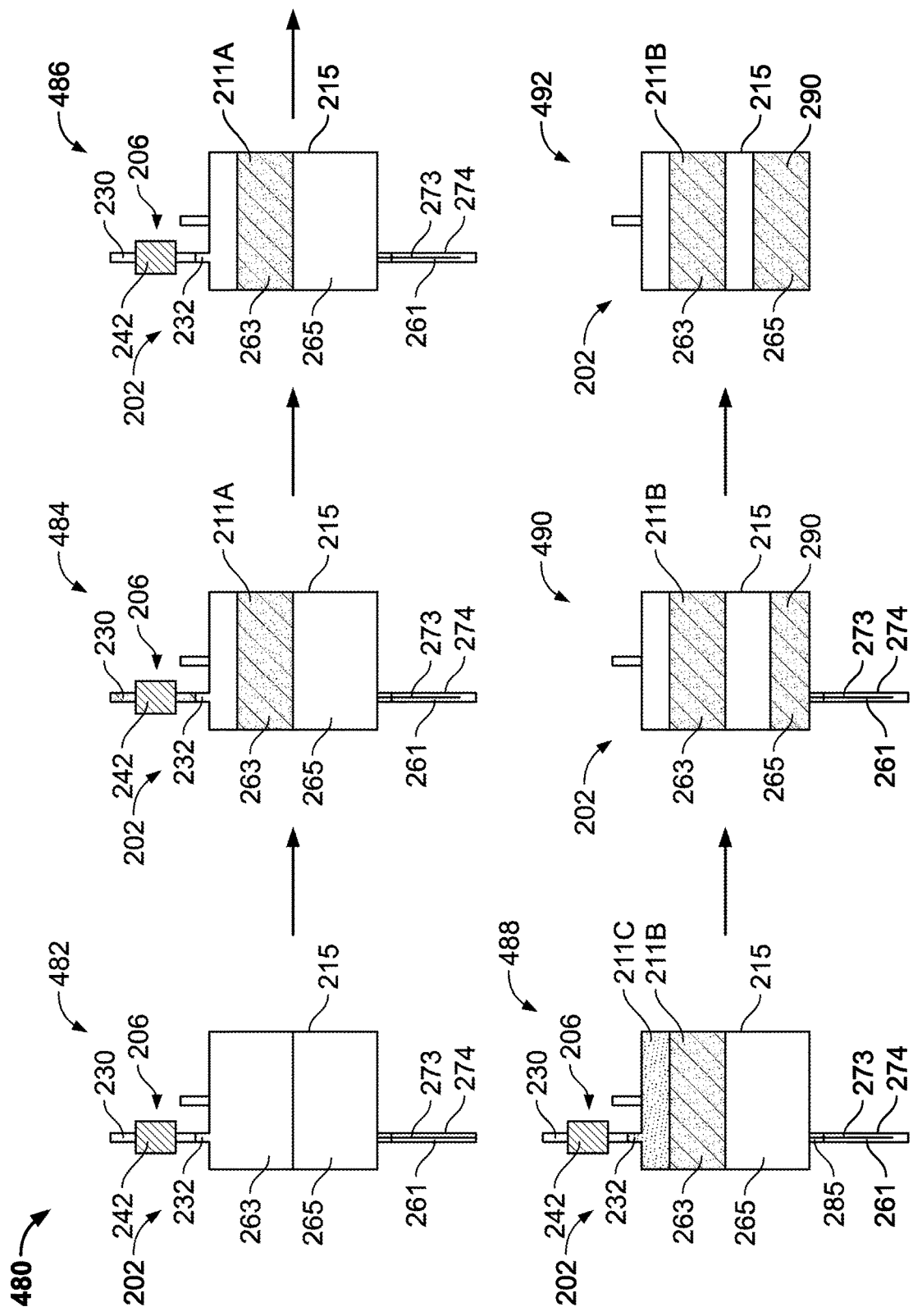
FIG. 24 is a third exemplary schematic for providing a sterile powder in a sealed chamber of a two-chamber product bag by lyophilization in accordance with the teachings of the present disclosure.

Turning to FIG. 24, an alternative method for providing a sterile powder in a sealed product bag by lyophilizing is illustrated. The process 480 involves a multi-chamber product bag, which may be the product bag 202 of FIG. 3B, involving an integrated vapor release member and filter assembly 206.

At an initial phase 482, an empty multi-chamber product bag 202 is provided, which includes a bladder 215, a stem 230 containing a filter 242, a port 232 fluidly connecting the stem 230 to the bladder 215, and a vapor release member 206 (which, in this example, includes the stem 230 and filter 242) fluidly connected to the bladder 215. At a filling phase 484, the method includes filling the product bag 202 with a liquid solution 211A through the filter 242. The product bag 202 is a liquid-filled product bag 202 at phase 486 when the bladder 215 contains the liquid solution 211A. At a lyophilization phase 488, the method includes removing a liquid of the liquid-filled product bag 202 by lyophilizing the liquid-filled product bag 202. During lyophilization, the frozen liquid of the liquid-filled product bag 202 sublimes to a vapor 211C, which is then removed from the bladder 215 by passing through the filter 242 of the vapor release member 206. In another embodiment, the vapor 211C may be released through a separate or different type of vapor release member. After lyophilization is complete, the product bag 202 is a powder-filled product bag 202 when the bladder 215 contains a powder concentrate 211B.

After removing the liquid, the method includes sealing the powder-filled product bag 202 at the port 232, and removing the stem 230 containing the filter 242 from the powder-filled product bag 202. Prior to a diluent filling phase 490, the method may include performing an integrity test on the filter 242 to ensure that the filter 242 adequately filtered the liquid solution during the filling phase 482, and that the powder-filled chamber 263 contains a sterile powder concentrate 211B. As discussed previously, the method may include correlating an integrity of the powder concentrate 211B of the powder-filled chamber 263 to an integrity of the filter 242 based on an outcome of the integrity test.

At the diluent filling phase 490, the method includes filling a second chamber 265 of the bladder 215 with a diluent 290 through a diluent filter 273 disposed within a diluent stem 274. A diluent port 285 fluidly connects the diluent stem 274 with the second chamber 265 and the second chamber 265 is fluidly sealed from the chamber 263 containing the powder 211B. The second chamber 265 is a liquid-filled second chamber 265 when the second chamber 265 contains the diluent 290. The method may include sealing the liquid-filled second chamber 265 at the diluent port 285 and removing the diluent stem 274 from the product bag 202 after completion of the diluent filling phase 490. After removing the diluent stem 274, the method may include performing an integrity test on the diluent filter 273 to ensure that the diluent filter 273 adequately filtered the diluent 290 during the filling phase 490, and that the diluent-filled chamber 265 contains a sterile diluent 290. At the integrity testing phase 492, the method includes correlating an integrity of the diluent 290 of the diluent-filled chamber 265 to an integrity of the diluent filter 273 based on an outcome of the integrity test.

The processes shown in FIGS. 22-24 are merely illustrative of the disclosed method performed on three different example product bags 101, 203, and 202, but each method may include a number of variations. For example, a diluent may be added directly to a powder-filled chamber instead of a separate chamber to reconstitute the concentrated drug. In another example, the filter assembly may act as both the solution filter and a diluent filter. The method may also apply to any product bag where the vapor release member is a one-way valve, a porous product bag, or an integrated filter with a first filter assembly. For example, the process 480 may be applied to the product bag 201 of FIG. 3A, and instead of a filter assembly 206 which releases a vapor during lyophilizing, the product bag 201 includes a different and/or separately configured vapor release member, such as a one-way valve 205.

Figure 25:
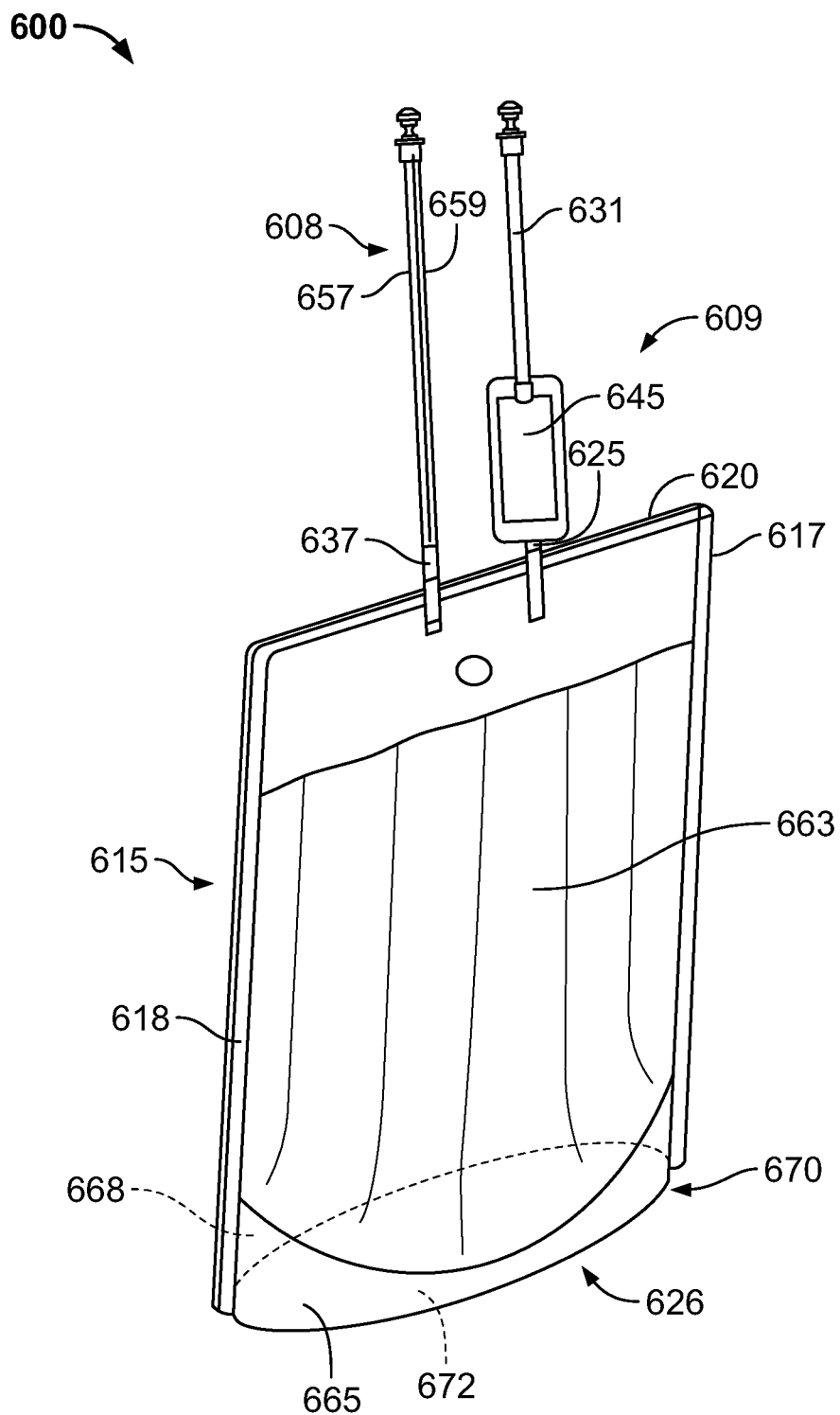
FIG. 25 is a perspective view of a product bag representative of any of the product bags of FIGS. 1-4A having a built-in support structure in accordance with the teachings of the present disclosure.

To enhance efficiency of the freeze-drying process (e.g. freeze-drying large batches of solution-filled product bags or decreasing assembly and processing time), various carriers, inherent bag features, and or methods may be provided. For example, a batch of product bags, such as a batch of the product bag 600 depicted in FIG. 25 may be lyophilized together in a single chamber of a freeze-drying machine. FIG. 25 illustrates a free-standing product bag 600 supporting its weight with a bladder 663, filter assembly 608, and vapor release member 609 oriented in an upright position. The product bag 600, which may be the product bag of any of the previous examples of FIGS. 1-4B with a single chamber or multiple chambers, includes a top portion 620, a bottom portion 626, and edge portions 617 and 618 that define the bladder 663. The edge portions 617 and 618 connect the top and bottom portions 620 and 626 of the bag 600 and surround the fillable pouch of the bladder 663. The bag 600 may include at least two layers of material defining opposing walls 665 and 668, which are sealed together at the top portion 620 and flare outwardly at the bottom portion 626 to form an expandable structure 670. The expandable structure 670 includes an end wall 672 oriented perpendicular to an upright orientation of the product bag 600, which is shown in FIG. 25. The end wall 672 is adapted to prop the bladder 663 on a horizontal surface and support the weight of the product bag 600, filtration system, and contents of the product bag 600. In this embodiment, the filter assembly 608 and the vapor release member 609 are connected to the bladder 663 at the top portion 620 of the bag 600. This arrangement permits the bag 600 to sit upright on a shelf or bin in a freeze-drying machine or in storage. A diluent filter or third filter (not shown) may be attached to the top portion 620 of the product bag 600 or may be attached to the edge or bottom portions 617, 618, or 626 of the bag 600 without interfering with the free-standing capabilities of the expandable structure 670. The expandable structure 670 may collapse so that the product bag 600 is substantially flat when the bladder 663 is empty or when the bag 600 lies horizontally for shipping and/or storage.

In another schematic, FIG. 26 shows how identical product bags 650A and 650B, containing the same amount of concentrate, may expand differently when subjected to the high temperature and pressure changes involved in lyophilization. The first product bag 650A is oriented on one of its sides when the product bag 650A is processed in a freeze-drying machine, and the other bag 650B is contained within a rigid container 670 during lyophilization. The vapor release member 654 of each bag 650A and 605B is generally parallel relative to a horizontal surface of a bin or shelf of the freeze-drying machine.

Without additional external constraints or barriers, the bladder 652 of the product bag 650A expands like a balloon to a maximum volume permitted by the bag material. A well 660A formed at one of the sides of the bladder 652 collects a solution that is to be lyophilized, and forms the shape of a powder concentrate cake 662A. The well 660A defines a first depth $D_A$ and a first surface area $S_A$ of the concentrated cake 662A. By comparison, the product bag 650B disposed within the rigid container 670 provides additional structural limitations to the expansion of the bladder 652, so that the bladder 652 may only expand to, at most, the interior dimensions of the container 670 during lyophilization. A well 660B formed in the product bag 650B defines a second depth $D_B$ and a second surface area $S_B$ of the concentrated powder cake 660B, where the second depth $D_B$ is less than the first depth $D_A$, and the second surface area $S_B$ is greater than the first surface area $S_A$. The larger surface area of the second cake 660B, which is representative of the larger surface area of the solution collected in the second bag 650B prior to lyophilization, may increase the rate of sublimation. Additionally, the rigid container 670 provides additional pressure to the product bag 650B, which may increase the rate of mass transfer through the vapor release member 654. In another embodiment, the container may hold the product bag in a vertical or angled orientation relative to the horizontal surface of the bin of the freeze-drying machine to increase process efficiency or to achieve a desired end product. In this way, FIG. 26 illustrates how a particular orientation of the product bag within a freeze-drying chamber may improve lyophilization efficiency and reduce processing time. Additionally, the rigid container 670 may allow for multiple product bags to be lyophilized together.

The disclosed methods and containers provide a number of advantages over known lyophilization methods and techniques. For example, the pre-sterilized chamber integrity of the bladder is never breached in a manner that would expose the container to environmental microbial contamination and/or particulate. This advantage is particularly useful for methods involving infused intravenous solutions that require stringent sterility and USP particulate product requirements. Moreover, because the environment of the container is pre-sterilized, a user would not be required to spend the time and costs associated with meeting and maintaining strict environmental sterility and other regulatory standards for filling the containers. The filling process does not require sourcing or manufacturing of sterile APIs prior to container filling, which may be particular beneficial for pharmaceuticals that are not amenable to aseptic sterile crystallization or filtration (e.g. biologics). Additionally, because the method and product bags of the present disclosure include liquid filling of the solution into the product bag, a user can exercise more precise control of lower drug concentrations and can easily prepare multi-component mixtures. Another advantage is that the disclosed method and container eliminate drug dust control requirements and risks associated with bulk powder handling, including toxic exposure of concentrated powders to handlers known to cause cancer. Users may also more readily sterilize pharmaceuticals that cannot be sterilized by steam or heat processes. Moreover, because the diluent can be provided to the bag on-demand, the sterility and integrity of the concentrate over the course of shipping and storing the product bag is no longer a concern.

In view of the foregoing, it should be appreciated that the various embodiments described herein provide examples of various devices, systems, and methods constructed in accordance with the principles of the present disclosure. These embodiments are not meant to be exclusive embodiments, but rather, any of the embodiments can be modified to include any one or more features of any of the other embodiments. As such, it should be appreciated that the examples provided herein are not exhaustive and the various features are interchangeable with each other, as well as with features not specifically disclosed but understood by a person having ordinary skill in the art.

What is claimed is:

1. A sterile solution product bag for lyophilizing, the product bag comprising:
   a bladder;
   a first stem having a first stem inlet end and a first stem outlet end, the first stem outlet end fluidly connected to the bladder and the first stem inlet end adapted to receive a liquid for introduction into the bladder;
   a first filter disposed in-line with the first stem, the first filter having a first filter membrane, a first filter open end, and a first filter closed end, the first filter closed end disposed between the first stem inlet end and the first stem outlet end and the first filter open end disposed in proximity to the first stem inlet end, the first filter arranged to sterilize the liquid as it passes through the first filter and into the bladder;
   a second stem having a second stem inlet end and a second stem outlet end, the second stem inlet end fluidly connected to the bladder and adapted to receive a vapor resulting from lyophilization of the liquid in the bladder;
   a second filter disposed in-line with the second stem, the second filter having a second filter membrane, a second filter open end, and a second filter closed end, the second filter open end disposed in proximity to the second stem inlet end.

2. The product bag of claim 1, wherein the bladder includes a first chamber and a second chamber, the first chamber fluidly isolated from the second chamber by a seal, and
   wherein the first stem outlet end and the second stem inlet end are in fluid communication with the first chamber of the bladder.

3. The product bag of any one of claim 1, comprising a third stem having a third stem inlet end and a third stem outlet end, the third stem outlet end fluidly connected to the bladder;
   a third filter disposed in-line with the third stem, the third filter having a third filter membrane, a third filter open end, and a third filter closed end, wherein the third filter open end is disposed in proximity to the third stem inlet end.

4. The product bag of claim 1, comprising
   a top portion, a bottom portion, and an edge portion connecting the top and bottom portions such that the top, bottom, and edge portions surround the bladder, the bottom portion including an expandable structure adapted to support the bladder, the first stem, and the second stem in an upright orientation relative to a horizontal surface, and
   wherein the first stem and the second stem are connected to the bladder at the top portion.

5. The product bag of claim 1, comprising a wall defining the bladder, the wall including a porous material having a pore size in a range of approximately 0.5 nm to approximately 230 nm, the pores adapted to expand during lyophilization to permit vapor formed in the bladder to pass through the pores.

6. The product bag of claim 1, wherein at least one of the first filter membrane and the second filter membrane has a nominal pore size in a range of approximately 0.1 µm to approximately 0.5 µm, wherein the at least one filter membrane includes a walled hollow fiber with pores residing in the wall.

7. A sterile solution container for lyophilization, the container comprising:
   a bladder,
   a stem having an inlet end and an outlet end, the outlet end in fluid communication with the bladder,
   a first filter comprising a first filter membrane, a first filter open end, and a first filter closed end, the first filter closed end disposed between the inlet end and the outlet end of the stem, the first filter membrane adapted to filter a liquid solution introduced through the inlet end of the stem to fill the bladder with a sterile liquid solution; and
   a vapor release member in fluid communication with the bladder and adapted to release a vapor from the bladder during lyophilization of the liquid solution while containing a powder product within the bladder, the vapor release member comprising a second filter having a second filter membrane, a second filter open end, and a second filter closed end, the second filter open end disposed in proximity to the bladder.

8. The container of claim 7, wherein the vapor release member further comprises a second stem having a second stem inlet end and a second stem outlet end, the second stem inlet end fluidly connected to the bladder, the second filter open end disposed in proximity to the second stem inlet end.

9. The container of claim 7, wherein at least one of the first filter membrane or the second filter membrane has a nominal pore size in a range of approximately 0.1 µm to approximately 0.5 µm, wherein the filter membrane includes a walled hollow fiber with pores residing in the wall.

10. A method of providing sterile powder in a sealed container by lyophilization, the method comprising:
    filling a chamber of a container with a liquid solution through a first filter, the container including a bladder defining the chamber, a first stem containing the first filter, a second stem containing a second filter, a first port fluidly connecting the first stem to the chamber of the bladder, a second port fluidly connecting the second stem to the chamber of the bladder, wherein the container is a liquid-filled container when the chamber of the bladder contains the liquid solution;
    after filling, sealing the liquid-filled container at the first port;
    removing the first stem containing the first filter from the liquid-filled container; and
    removing liquid of the liquid-filled container by lyophilizing the liquid-filled container, wherein the liquid is removed through the second stem, wherein the container is a powder-filled container when the chamber of the bladder contains powder after lyophilizing.

11. The method of claim 10, including, after removing liquid, sealing the powder-filled container at the second port; and
    removing the second stem containing the second filter.

12. The method of claim 10, including, after removing the first stem, performing an integrity test on the first filter; and
    correlating an integrity of the liquid solution of the liquid-filled container to an integrity of the first filter based on an outcome of the integrity test.

13. The method of claim 10, including, after removing the second stem, performing an integrity test on the second filter; and
    correlating an integrity of the sterile powder of the powder-filled container to an integrity of the second filter based on an outcome of the integrity test.

14. The method of claim 10, wherein removing liquid includes freeze-drying the liquid-filled container in a pressurized lyophilization chamber.

* * * * *